(12) United States Patent
Domalaon et al.

(10) Patent No.: US 11,806,320 B2
(45) Date of Patent: Nov. 7, 2023

(54) ISOPROTERENOL COMPOSITIONS AND METHODS

(71) Applicant: ENDO VENTURES LIMITED, Dublin (IE)

(72) Inventors: Ronald Domalaon, Raritan, NJ (US); Jinjiang Li, Monmouth Junction, NJ (US); Tushar Hingorani, Bridgewater, NJ (US); Kumaresh Soppimath, Skillman, NJ (US)

(73) Assignee: ENDO VENTURES LIMITED, Dublin (IE)

( * ) Notice: Subject to any disclaimer, the term of this patent is extended or adjusted under 35 U.S.C. 154(b) by 0 days.

(21) Appl. No.: 17/179,078

(22) Filed: Feb. 18, 2021

(65) Prior Publication Data

US 2021/0259994 A1 Aug. 26, 2021

Related U.S. Application Data

(60) Provisional application No. 62/978,624, filed on Feb. 19, 2020.

(51) Int. Cl.
| | |
|---|---|
| *A61K 31/137* | (2006.01) |
| *A61K 9/08* | (2006.01) |
| *A61K 47/54* | (2017.01) |
| *A61J 1/14* | (2023.01) |
| *A61L 2/00* | (2006.01) |

(52) U.S. Cl.
CPC .............. *A61K 31/137* (2013.01); *A61K 9/08* (2013.01); *A61K 47/547* (2017.08); *A61L 2/0017* (2013.01); *A61J 1/14* (2013.01); *A61L 2202/21* (2013.01)

(58) Field of Classification Search
None
See application file for complete search history.

(56) References Cited

U.S. PATENT DOCUMENTS

| | | | | |
|---|---|---|---|---|
| 9,511,033 B2* | 12/2016 | Myers | ................. | A61K 47/183 |
| 2002/0169199 A1* | 11/2002 | Gruber | ................. | A61K 9/0019 |
| | | | | 514/474 |
| 2009/0041800 A1* | 2/2009 | Woiwode | ................ | A61P 25/32 |
| | | | | 424/195.15 |
| 2014/0275144 A1* | 9/2014 | Cuine | ...................... | A61K 9/08 |
| | | | | 514/282 |
| 2014/0275202 A1* | 9/2014 | Schmitz | .................. | A61K 9/19 |
| | | | | 514/418 |
| 2016/0009680 A1* | 1/2016 | Kawakami | ........... | C07D 487/04 |
| | | | | 540/562 |
| 2020/0078326 A1* | 3/2020 | Jacobsen | .................. | A61K 9/08 |

FOREIGN PATENT DOCUMENTS

| | | | | |
|---|---|---|---|---|
| CA | 643376 A | 6/1962 | | |
| CA | 659429 A | 3/1963 | | |
| EP | 1674084 B1 * | 9/2009 | ......... | A61K 31/137 |
| WO | WO-2019150381 A1 * | 8/2019 | ......... | A61K 31/137 |

OTHER PUBLICATIONS

Ghaibi et al. Hospital Pharmacy 2014 49(2):136-163 (Year: 2014).*
Adult Intravenous Medications (med.umkc.edu/docs/em/IV_Med_Reference.pdf 2008 (Year: 2008).*
Waterman et al. International Journal of Pharmaceutics 2005 293:101-125 (Year: 2005).*
Leighton et al., "Isoproterenol is an Effective Marker of Intravenous Injection in Laboring Women," Anesthesiology, 1989; 71:206-209.
Isuprel Prescription Information Sheet by Hospira, Inc., Lake Forest, IL, Mar. 2013; 6 pgs.

* cited by examiner

*Primary Examiner* — Melissa S Mercier
*Assistant Examiner* — Caralynne E Helm
(74) *Attorney, Agent, or Firm* — ArentFox Schiff LLP

(57) ABSTRACT

Storage stable aqueous ready-to-administer formulations comprising isoproterenol are presented with desirable stability characteristics. In preferred aspects, formulations are terminally sterilized and packaged in a suitable format, such as a polymeric bag with metalized overwrap and include a non-contact oxygen scavenger.

18 Claims, 2 Drawing Sheets

ISOPROTERENOL COMPOSITIONS AND METHODS

This application claims priority to our US Provisional Patent Application with the Ser. No. 62/978,624, which was filed Feb. 19, 2020, and which is incorporated by reference herein.

FIELD OF THE INVENTION

The present disclosure relates to isoproterenol-containing pharmaceutical compositions and methods for same, especially as it relates to storage stable compositions of isoproterenol and methods therefor.

BACKGROUND OF THE INVENTION

The background description includes information that may be useful in understanding the present disclosure. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Isoproterenol is a synthetic sympathomimetic catecholamine with potent agonist activity towards beta-adrenergic (beta1 and beta2) but very low affinity towards alpha-adrenergic receptors. Intravenous administration of isoproterenol in human lowers peripheral vascular resistance due to its ability to relax almost all varieties of smooth muscles in the body, but its action is most pronounced on bronchial and gastrointestinal smooth muscles. Isoproterenol is used to treat bradycardia (slow heart rate), heart block and Adam-Stokes syndrome. It is also administered in emergency situations to patients suffering cardiac arrest until electric shock is available. Furthermore, isoproterenol is used to alleviate bronchospasm during anesthesia. It is also used as an adjunct agent for the treatment of hypovolemic shock, septic shock and cardiogenic shock due to Isoproterenol's function to relax smooth muscles. In human, isoproterenol poses less risk to induce hyperglycemia than epinephrine. Isoproterenol is a relatively poor substrate of monoamine oxidase (MOA) and is not taken up by sympathetic neurons to the same extent as epinephrine and norepinephrine. Therefore, the duration of action of isoproterenol may be relatively longer than that of epinephrine, although still brief.

Chemically, isoproterenol (4-{1-hydroxy-2-[(propan-2-yl)amino]ethyl}benzene-1,2-diol, hydrochloride, also known as isoprenaline) is a synthetic catecholamine that comprises a catechol moiety, benzylic alcohol and a secondary amine linking an isopropyl moiety to the benzylic core of the molecule. The benzylic carbon attached to an alcohol group is a chiral center. The (R)-enantiomer of Isoproterenol is reportedly ~90 times more potent than its (S)-enantiomer. However, known pharmaceutical compositions of isoproterenol are racemic.

Isoproterenol hydrochloride has a solubility of 1 g in 3 mL water, 1 g in 50 mL ethanol (95%), is sparingly soluble in alcohol, less soluble in dehydrated alcohol, and insoluble to organic non-polar solvents such benzene, chloroform and ether. Isoproterenol is incompatible with sodium bicarbonate and aminophylline and is unstable at alkali conditions.

Unfortunately, isoproterenol is heavily susceptible to oxidation (pH-, photo- and metal-catalyzed), isomerization and nucleophilic (condensation) reactions. Moreover, isoproterenol is also unstable to prolonged exposure to light. Consequently, numerous methods have been developed to maintain or increase chemical stability of isoproterenol. For example, WO 2019/150381 describes methods and systems that reduce dissolved oxygen content and that maintain oxygen in the headspace of packaged formulations at a relatively low level. In another example, isoproterenol formulations were stabilized via formation of an addition salt and use of ascorbic acid as antioxidant as is shown in CA 643,376. In still another example, anhydrous solvents with fluorohydrocarbons as stabilizing components are used as taught in CA 659,429. While such compositions provide at least some advantages with regard to storage stability, they are typically not suitable for use in ready-to-use formulations.

Thus, even though various isoproterenol compositions are known in the art, all or almost all of them suffer from various disadvantages. Consequently, there is a need to provide improved compositions and methods that provide isoproterenol formulations with desirable stability, particularly where such formulations are ready-to-administer.

SUMMARY OF THE INVENTION

Compositions and methods are presented that afford desirable stability for isoproterenol, and especially for ready-to-administer injectable formulations. Most typically, contemplated formulations will comprise isoproterenol at concentrations of between about 1-10 mcg/mL in low-strength buffer systems at a pH range of about pH 3.0-4.5. Where desired, additional non-contact antioxidants and metal chelators are included to further enhance chemical stability, particularly where such formulations are terminally sterilized.

In one aspect of the inventive subject matter, the inventors contemplate a liquid sterile ready-to-administer pharmaceutical composition that comprises a buffered aqueous solution comprising isoproterenol at a concentration suitable for intravenous administration without further dilution, wherein the buffered aqueous solution has a pH range of between 3.0 and 4.5 and wherein the buffer has a concentration of equal or less than 10 mM. In preferred embodiments, the solution further comprises a chelating agent and a tonicity agent, and the ready-to-administer composition contains, after storage over at least three weeks at 60° C., equal or less than 2.5% or less than 2.0% or less than 1.5% or less than 1.0% of total impurities formed from degradation of the isoproterenol. In further contemplated aspects, the composition is antioxidant free.

In some embodiments, the isoproterenol is present at a concentration of between 1-20 mcg·mL or 1-10 mcg/mL, for example, at a concentration of 4.0±0.2 mcg/mL. In further embodiments, the buffered aqueous solution has a pH range of between 3.5 and 4.2, or the buffered aqueous solution has a pH of 4.0±0.2. Typically, the buffer has a concentration of equal or less than 1 mM, such as 1 mM or 0.25 mM. It is further especially contemplated that the buffer is a tartrate buffer. In other aspects, the chelating agent is ethylenediamine tetraacetic acid (EDTA) and may be present at a concentration of equal or less than 10 mcg/mL, for example, a concentration of 5±2 mcg/mL. Most typically, but not necessarily, the tonicity agent is NaCl and is present in an amount of 9±2 mg/mL.

In further embodiments, the ready-to-administer composition is an autoclaved composition, which may be packaged into a flexible polymeric container (e.g., at a volume of 100 mL) or glass vial. Furthermore, the flexible polymeric container may be contained in a secondary container, and a non-contact oxygen absorber may be placed into a space between the flexible polymeric container and the secondary container.

Therefore, in further contemplated embodiments, a liquid sterile ready-to-administer pharmaceutical composition will essentially consist of a buffered aqueous solution comprising isoproterenol at a concentration of between 1-10 mcg/mL, wherein the buffered aqueous solution has a pH range of between 3.0 and 4.5 and wherein the buffer is a tartrate buffer and has a concentration of equal or less than 10 mM. Most typically, the solution further comprises ethylenediamine tetraacetic acid (EDTA) as a chelating agent at a concentration of equal or less than 10 mcg/mL and NaCl as a tonicity agent in an amount of 9±2 mg/mL, and the ready-to-administer composition contains, after storage over at least three weeks at 60° C., equal or less than 2.0% or equal or less than 1.5% or equal or less than 1.0% of total impurities formed from degradation of the isoproterenol.

Preferably, such the isoproterenol in such composition is present at a concentration of 4.0±0.2 mcg/mL, and/or the buffered aqueous solution has a pH range of between 3.5 and 4.2 (e.g., pH of 4.0±0.2). It is further contemplated that the buffer has a concentration of equal or less than 1 mM (e.g., 1 mM or 0.25 mM), and/or that the chelating agent is present at a concentration of 5±2 mcg/mL. Moreover, it is generally preferred that the ready-to-administer composition is an autoclaved and antioxidant-free composition. However, it is also contemplated that the ready-to-administer composition is a filter sterilized and antioxidant-free composition.

Viewed from a different perspective, the inventors also contemplate a kit comprising the liquid sterile ready-to-administer pharmaceutical composition presented herein, wherein the composition is typically packaged in a primary container at a volume of between 10 mL and 150 mL (e.g., 100 mL). It is further generally preferred that the primary container is disposed in a secondary container, and that the secondary container comprises a metal (e.g., metallized plastic or metal film coupled to plastic or is a metal film). Advantageously, the kit will further include a non-contact oxygen absorber disposed in a space between the primary container and the secondary container.

Therefore, in still another aspect of the inventive subject matter, a method of preparing a liquid sterile ready-to-administer pharmaceutical composition will include a step of formulating a liquid parenteral composition that contains in a buffered aqueous acidic solution isoproterenol, a chelating agent, and a tonicity agent, wherein the isoproterenol is present in the composition at a concentration suitable for intravenous administration without further dilution, and wherein the buffered aqueous acidic solution has a pH range of between 3.0 and 4.5, and wherein the buffer has a concentration of equal or less than 10 mM. In a further step, the liquid parenteral composition is sterilized (e.g., via autoclaving or sterile filtration) to so obtain the liquid sterile ready-to-administer pharmaceutical composition. Most typically, such ready-to-administer composition contains, after storage over at least three weeks at 60° C., equal or less than 2.5% or equal or less than 2.0% or less than 1.5% or less than 1.0% of total impurities formed from degradation of the isoproterenol. Preferably, the composition will be antioxidant free.

With respect to the isoproterenol concentration, the type and concentration of the buffer, the chelator, and the tonicity agent, the same considerations as noted above apply. Likewise, contemplated methods may further include a step of packaging the composition into a flexible polymeric container, which may be further packaged into a secondary container, preferably with a non-contact oxygen absorber placed in a space between the flexible polymeric container and the secondary container.

In still another aspect of the inventive subject matter, the inventors also contemplate a method of treating a subject in which, without prior dilution, the liquid sterile ready-to-administer pharmaceutical composition presented herein is administered to a subject in need thereof. Therefore, a sterile ready-to-administer pharmaceutical composition as presented herein is used for treatment of a condition that is responsive to isoproterenol, wherein the composition is administered to the subject without prior dilution.

Various objects, features, aspects, and advantages will become more apparent from the following detailed description of preferred embodiments, along with the accompanying drawing in which like numerals represent like components.

DETAILED DESCRIPTION

The inventors have now discovered that storage stable, aqueous, and ready-to-administer isoproterenol formulations can be prepared with a desirable stability profile. Moreover, the formulations presented herein can be terminally sterilized and packaged in a format that maintains protection form light and oxygen ingress and as such further enable extended storage stability. Reference to the term "isoproterenol" herein is meant to include isoproterenol and all pharmaceutically acceptable salt forms thereof (e.g., isoproterenol hydrochloride).

More specifically, the inventors contemplate that formulations can be prepared that will exhibit after sterilization (e.g., autoclaving) and storage at 60° C. for two weeks less than 6%, more preferably less than 5%, even more preferably less than 4%, and most preferably less than 3% or less than 2% of total impurities due to degradation of isoproterenol as determined by HPLC-UV. Most notably, such formulations are expected to be stable over extended periods at very low concentrations of antioxidants (e.g., at least 1 month, or at least two months, or at least three months), even at elevated storage temperatures (e.g., accelerated storage conditions such as 40° C. and 75% relative humidity (+/−5%)). Moreover, such formulations are contemplated to be subjected to thermal sterilization, and particularly autoclaving to sterility (e.g., over at least 5 min, or at least 10 min, or at least 15 min, or at least 30 min at 121° C.), without substantial increase in degradation or change in enantiomeric configuration.

Figure 1:
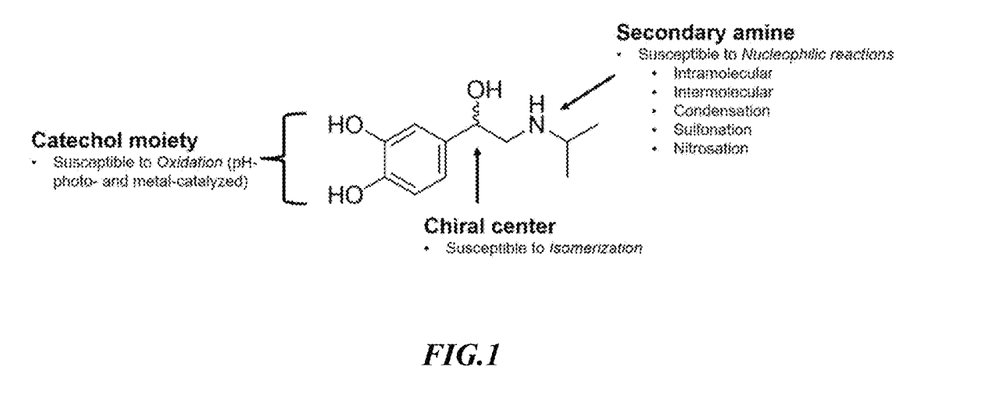
FIG. 1 schematically depicts various reactive groups in isoproterenol that can be involved in various degradation pathways.

Such stability is particularly remarkable in view of the diverse pathways through which isoproterenol can degrade. As is described in more detail below, isoproterenol can degrade though various oxidative pathways and nucleophilic reactions due to the presence of various reactive functional moieties in isoproterenol. More specifically, the structure of isoproterenol allows the formation of 6-/5-membered ring aminochrome degradation products by cyclization reactions, where such reaction cascades may be initiated by oxidation or nucleophilic attack: The catechol moiety is labile to oxidation reactions that may be pH-, photo- or metal-catalyzed. The benzylic carbon linked to an alcohol group, being a chiral center, is susceptible to racemization at strong acidic pHs. The secondary amine group can act as a nucleophile in cyclization reactions but can also undergo intermolecular attack on other electrophilic centers (e.g., excipients/buffers) in solution at alkali conditions and/or heat. An exemplary overview of the chemical lability of isoproterenol is shown in FIG. 1, and the various degradation mechanisms/pathways are addressed in more detail below.

Oxidative degradation: Isoproterenol contains a catechol (benzene-1,2-diol) functional group that is susceptible to oxidation leading to the formation of quinone-intermediates that subsequently transform into N-Isopropyl-noraminochrome (an aminochrome) via cyclization cascades. Oxidation, via free radical oxygen, may be triggered by pH, light (photon) and/or metal ions. The presence of reactive oxygen species (free radicals) activates one of the phenolic alcohols of isoproterenol resulting to a short-live semiquinone intermediate followed by the formation of an ortho-quinone. The ortho-quinone can be generated by radical propagation reaction of two semiquinone intermediates, but as well as reaction of a semiquinone to another radical source. The secondary amine of isoproterenol can then undergo an intramolecular nucleophilic attack to yield N-isopropylnoraminochrome.

pH-catalyzed Oxidation: Isoproterenol is known to be unstable at alkali conditions. Phenolic compounds (such as isoproterenol) may undergo degradation/transformation in the presence of oxygen, termed autooxidation. The activation of phenolic compounds follows Equation 1.

Equation 1. Equilibrium for phenolic autooxidation initiation step

Most phenolic compounds at physiological conditions (pH of 7, etc.) are in cationic form, and that their reduction potential at protonated state renders the equilibrium thermodynamically infeasible where the equilibrium lies well to the left. Following Le Chatelier's principle, the abundance of protons ($H^+$) in acidic to neutral conditions drives the autooxidation equilibrium to the left. Reduction potential of catechol-containing small organic molecules is typically $E_m$ (pH 7)+380 mV vs standard hydrogen electrode. For instance, the cationic form of isoproterenol is predominant at pH≤6. However, shifting the ionic population of isoproterenol into a predominantly neutral or anionic form (occur at pH>6) would affect its reduction potential and push the equilibrium to the right, generating reactive phenolic species that participates in cascades of oxidation reaction. Therefore, the inventors contemplate that pH values of 6 and greater should be avoided to minimize oxidation.

Metal-Catalyzed Oxidation: Metal ions, such as copper and iron, are known to catalyze the oxidation of labile organic compounds. For instance, ferrous ion ($Fe^{2+}$) can react with molecular oxygen to form hydrogen peroxide ($H_2O_2$) through a series of redox reactions. This reaction cascade leading to formation of highly reactive oxygen species is called Fenton reaction. The resultant activated oxygen at its excited state can then initiate the oxidation of isoproterenol. Cupric ion ($Cu^{2+}$) can also catalyze the degradation of Isoproterenol via redox reactions. Thus, the inventors contemplate to sequester any metal ions in solution to prevent metal-catalyzed oxidation, and especially contemplated agents include biocompatible chelating agents such as edetate disodium (EDTA) and citric acid.

Photooxidation: Catecholamines, such as isoproterenol, are known to be sensitive to photoreactions. Isoproterenol can undergo photooxidation upon direct absorption of UV & visible light. Absorption of photon (light) can energize the catechol hydroxyl moiety to an excited state leading to radical generation that then react with molecular oxygen. The superoxide radical anion ($O_2^{\cdot-}$) is generated, which is known to be involved in photo-catalytic degradation reactions. Consequently, the inventors contemplate that isoproterenol should be protected from prolonged light exposure to prevent the generation of free radicals.

Figure 2:
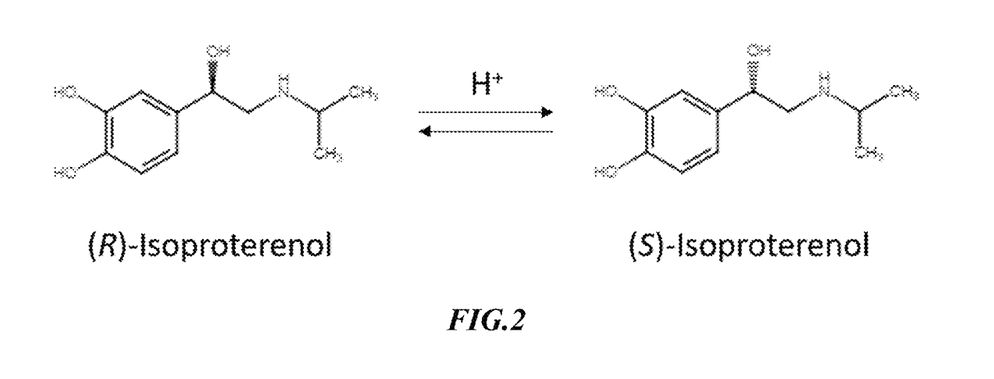
FIG. 2 depicts isomerization of isoproterenol.

Isomerization: The presence of a chiral center renders isoproterenol susceptible to isomerization. The active (R)-enantiomer, with an optical rotation of (−), isomerizes to a less potent (S)-enantiomer, with an optical rotation of (+), in solution as is shown in FIG. 2. The rate of isomerization is enhanced at strongly acidic conditions. At 1M HCl concentration, data for the acid-catalyzed racemization of catechol suggested that the para-alcohol substituent influence the reaction rate and that reaction proceeds via a quinoid-type intermediate formation in contrast to a $SN_1$-type (carbocation intermediate) reaction pathway. Therefore, highly acidic pH values are deemed problematic.

Nucleophilic reactions: Conditions that promote degradation via reaction of electron-rich compounds (nucleophile) to electron-loving compounds (electrophile) should be considered in drug product formulations. Nucleophilic degradation pathway results to a complex assortment of unwanted products that may incur more burden in the formulation development. Therefore, it is contemplated to avoid nucleophilic compounds in contemplated formulations. For isoproterenol, potential nucleophilic degradation pathways include condensation, sulfonation and nitrosation reactions as discussed below.

Pictet-Spengler and Maillard Condensation: Condensation reaction of catecholamines with carbohydrates is initiated by a nucleophilic attack of free amine to the reducing end of sugar yielding a reactive Schiff base. This reactive intermediate further degrades either via an intramolecular Pictet-Spengler cyclization reaction or Maillard reaction following an Amadori rearrangement. The molecular geometry, existing functional groups, pH and metal ions affect whether the Schiff base undergo either or both condensation reactions. Thermal activation is required to enhance the kinetics of this degradation pathway. pH also appears to play an important role to initiate condensation. Degradation of catecholamines in the presence of D-glucose at 90° C. for 3 hours was reportedly less at pH 5 relative to neutral and basic pHs. Since condensation reactions require an amine group to be unprotonated (to act as a nucleophile), acidic pH prevents the formation of a Schiff base intermediate by maintaining the amine at its protonated (cationic) form. Therefore, the inventors contemplate that this degradation pathway for the catecholamine isoproterenol may be minimized/prevented at more acidic pH values.

Sulfonation by bisulfite: Sulfites, bisulfites and metabisulfites had been extensively used in pharmaceutical formulations as antioxidants. However, sympathetic catecholamines such as epinephrine and related compounds have been reported to yield degradation products with sodium bisulfite in prolonged exposure at elevated temperatures. It was found that benzylic alcohols derivatives with hydroxyl functional group at the ortho- and para-position (for instance isoproterenol and epinephrine have para-hydroxybenzyl alcohol) react with bisulfite to form degradation products, while those with only meta-hydroxyl groups do not. This information suggests that sulfite-based antioxidants such as sodium bisulfite may not be suitable for formulations of isoproterenol.

Nitrosation: Pharmaceutical agents containing a secondary amine (tertiary amines to a much lesser extent) are susceptible to degradation via formation of N-nitroso compounds in the presence of nitrites or nitrates. Aside from the loss of biologically active composition, formation of N-nitroso degradation compounds even at trace levels may incur carcinogenicity to the drug product. Under mildly acidic solutions, nitrites and nitric acid form reactive nitrosonium ion ($NO^+$) carrier species ($N_2O_3$ in the case of nitrite) that consequently nitrosate secondary amines. Catecholamines such as epinephrine and isoproterenol possess a secondary amine and therefore is susceptible to nitrosation reactions. Therefore, the inventors contemplate that it is important to avoid the use of any nitrite or nitrate excipients and to ensure that the drug formulation contains no such impurities.

Figure 3:
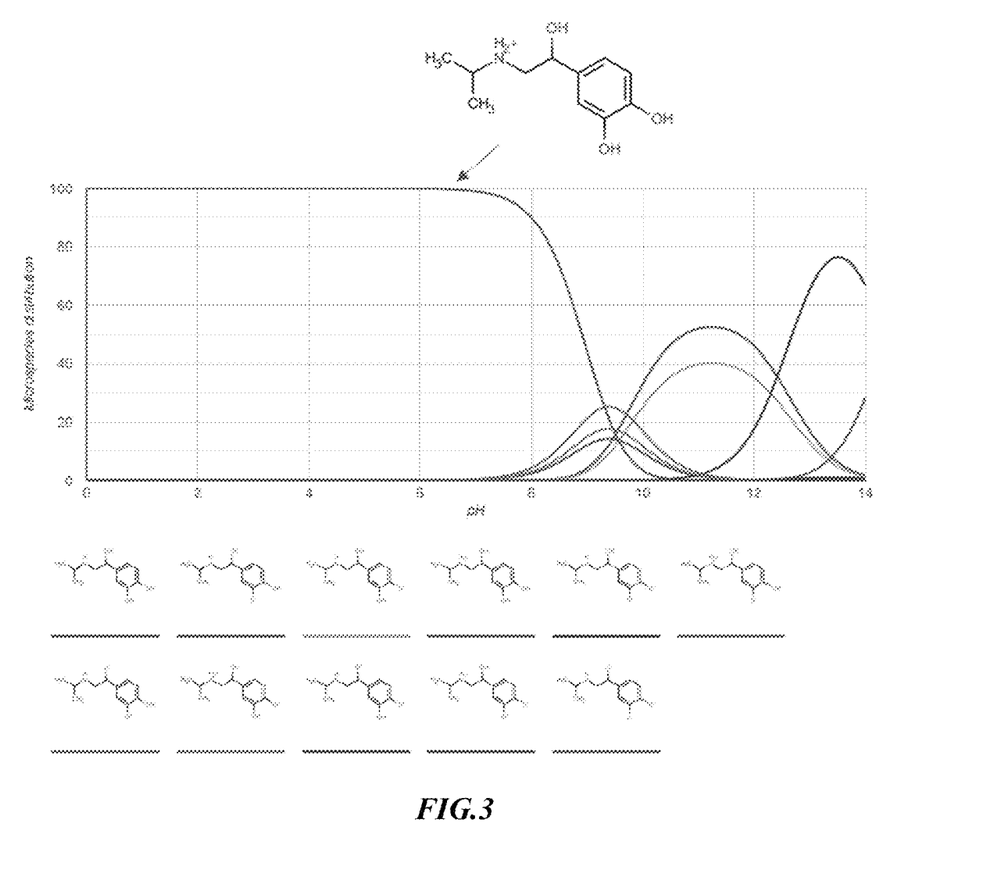
FIG. 3 depicts calculated occurrence of various ionic forms for isoproterenol as a function of pH.

Following further consequences of the chemical reactive nature of isoproterenol, the inventors generated a predicted population profile of isoproterenol's different ionic forms at different pH was using the Chemicalize program (URL: chemicalize.com) and exemplary results are shown in FIG. 3. Here, the cationic form of isoproterenol is predominant at pH values below 6. Identification of a suitable pH range is important since the cationic form of isoproterenol is preferred to be principal in solution to minimize potential cyclization and degradation reactions, as described above.

Based on the above and further considerations, the inventors therefore contemplate that aqueous formulations of isoproterenol will generally fall within a relatively narrow range of pH and will avoid a variety of components otherwise commonly used in pharmaceutical formulations. Moreover, to maintain proper pH ranges, the inventors contemplate use of buffer systems that will not interfere with chemical stability of isoproterenol. In addition, the inventors also contemplate that formulations will preferably contain one or more chelating agents and/or antioxidants, which will also not interfere with chemical stability of isoproterenol.

In one aspect of the inventive subject matter, one exemplary contemplated formulation has a composition as shown in Table 1. Advantageously, such composition has a total volume of 100 mL, is packaged in a flexible polymeric bag that is contained in a metallized overwrap with a non-contact oxygen scavenger disposed between the polymeric bag and the overwrap. Moreover, such formulation is terminally sterilized by autoclaving.

TABLE 1

| Ingredient | Function | Quantity per mL |
|---|---|---|
| Isoproterenol hydrochloride | Active pharmaceutical ingredient | 4.0 mcg |
| L-tartaric acid | Buffering agent | 37.5 mcg |
| Edetate disodium dihydrate (EDTA) | Metal chelating agent | 5.0 mcg |
| Sodium chloride | Isotonicity agent | 9.0 mg |
| 10N NaOH/HCl | pH adjuster | q.s. pH 4.0 |
| Water for Injection | Vehicle | q.s. 1 mL |

Of course, it should be appreciated that numerous modifications can be made to the above formulation to adjust to a particular need or preferred process. For example, and with respect to contemplated isoproterenol concentrations it is typically preferred that the isoproterenol is present in the formulation at concentration that is suitable for injection without further need for dilution before injection to a subject in need thereof. Therefore, suitable isoproterenol concentrations will be at least 0.1 mcg/mL, or at least 0.5 mcg/mL, or at least 1.0 mcg/mL, or at least 2.0 mcg/mL, or at least 4.0 mcg/mL, or at least 8.0 mcg/mL, or at least 10 mcg/mL, or at least 20 mcg/mL, or at least 40 mcg/mL, or even higher. Particularly where the formulation is intended for direct administration without prior dilution from a more concentrated form, contemplated concentrations will generally be equal or less than 20 mcg/mL, or equal or less than 15 mcg/mL, or equal or less than 10 mcg/mL, or equal or less than 8 mcg/mL, or equal or less than 6 mcg/mL, or equal or less than 4 mcg/mL, or equal or less than 2 mcg/mL, or equal or less than 1 mcg/mL.

Consequently, suitable concentration ranges for isoproterenol in the final formulation will be between 0.1 and 1 mcg/mL, or between 0.5 and 2.5 mcg/mL, or between 1 and 5 mcg/mL, or between 2.5 and 7.5 mcg/mL, or between 5.0 and 10 mcg/mL, or between 10 and 20 mcg/mL, or between 20 and 40 mcg/mL, or even higher. Therefore, suitable concentrations will be 1.0 mcg/mL, or 2.0 mcg/mL, or 3.0 mcg/mL, or 4.0 mcg/mL, or 5.0 mcg/mL, or 6.0 mcg/mL, or 7.0 mcg/mL, or 8.0 mcg/mL, or 9.0 mcg/mL, or 10.0 mcg/mL, and even higher. In still less preferred, but nevertheless contemplated aspects, the isoproterenol concentration may also be high enough to require dilution with a suitable diluent prior to administration (e.g., 50 mg/mL, or 100 mcg/mL, or 200 mcg/mL). It should be noted that these concentrations may also be approximate concentrations that have a variability of +/−5%, or +/−10%, or +/−15%, or +/−20% of the given value.

As already noted above, the isoproterenol concentrations contemplated herein will generally have an acidic pH which will generally be equal or less than 7.0, or equal or less than 6.5, or equal or less than 6.0, or equal or less than 5.5, or equal or less than 5.0, and more preferably equal or less than 4.5, or equal or less than 4.0, or equal or less than 3.5, or equal or less than 3.0, and in some cases even less. Thus, contemplated pH ranges will typically be between 3.0 and 4.5, or between 3.0 and 4.2, or between 3.0 and 4.0 or between 3.5 and 4.2, or between 3.5 and 4.5. For example, contemplated formulations may have a pH of 3.0+/−0.2, or may have a pH of 3.3+/−0.2, or may have a pH of 3.6+/−0.2, or may have a pH of 3.8+/−0.2, or may have a pH of 4.0+/−0.2, or may have a pH of 4.2+/−0.2, or may have a pH of 4.4+/−0.2, or may have a pH of 4.6+/−0.2. It is also preferred that the pH value will not significantly change over time, and contemplated pH differences between initial pH and pH after storage are equal or less than 0.3 pH units, equal or less than 0.25 pH units, equal or less than 0.2 pH units, equal or less than 0.15 pH units, equal or less than 0.1 pH units, equal or less than 0.1 pH units, or equal or less than 0.05 pH units (e.g., when stored at 60° C. for three weeks).

While numerous buffers and buffer systems including organic, inorganic, and amphoteric buffers are deemed suitable for use herein, it is generally preferred that the pH will be maintained by an organic buffer or buffer system. Therefore, especially contemplated buffer systems include formate, citrate, glycine, tartrate, acetate, and glutamate buffer systems, and especially tartrate, acetate, and glutamate buffer systems as shown in more detail below. However, in further contemplated aspects, suitable buffers also include various amphoteric buffers such as MOPS, HEPES, MES, Bis-TRIS, etc. In still further contemplated aspects, a buffer may also be entirely omitted.

Notably, selected buffers, and particularly tartrate, acetate, and glutamate buffer in the above pH range provided remarkable stability for the low concentrations of isoproterenol, especially when in combination with a chelator and a salt as discussed in more detail below. In further unexpected findings, the inventors discovered that tartrate buffer provided particularly improved stability for isoproterenol, even when compared to acetate and glutamate buffers as is also shown in more detail below. Moreover, the inventors also surprisingly discovered that the buffer strength has also a significant effect on stabilization of isoproterenol (see examples below). Therefore, especially contemplated buffer strengths will be relatively low, for example, equal or less than 50 mM, and more typically equal or less than 25 mM, or equal or less than 10 mM, or equal or less than 5 mM, or equal or less than 2 mM, or equal or less than 1 mM, or equal or less than 0.5 mM, or equal or less than 0.25 mM. For example, preferred buffers (and particularly tartrate buffers) will have a concentration of between about 0.1-0.4 mM, or between about 0.2-0.5 mM, or between about 0.4-0.8 mM, or between about 0.7-1.4 mM, or between about 1-2 mM, or between about 2-5 mM, or between about 5-10 mM, and in some cases higher. However, in preferred examples, the buffer strength is equal or less than 5 mM or 2 mM, such as 0.25 mM or 1.0 mM.

In still further contemplated aspects, the formulations presented herein will also include one or more chelating agents, and particularly metal ion chelators. For example, suitable chelators include various bicarboxylic acids, tricarboxylic acids, and aminopolycarboxylic acids such as ethylenediaminetetraacetic acid (EDTA), ethylene glycol-bis(β-aminoethyl ether)-N,N,N',N'-tetraacetic acid (EGTA), and penta(carboxymethyl)diethylenetriamine (DTPA), and salts and hydrates thereof. While not limiting to the inventive subject matter, it is contemplated that the metal ion chelators will slow down both the baseline and metal ion-stimulated degradation of isoproterenol. Remarkably, the inventors unexpectedly observed that the desirable effect of the chelators was observable at considerably low concentrations of the chelator, especially where the formulation was subjected to terminal sterilization (e.g., autoclaving). For example, reduction of the baseline and metal ion-stimulated degradation of isoproterenol was observed at chelator concentrations of between 1 mcg/mL and 10 mcg/mL (e.g., at 1 mcg/mL, or 5 mcg/mL, or 10 mcg/mL), between 10 mcg/mL and 20 mcg/mL, between 20 mcg/mL and 50 mcg/mL, and in some cases even higher. Notably, and as shown in more detail below, an optimum stabilization effect could be observed among very low concentrations of chelator. Interestingly, the chelators, and especially the aminopolycarboxylic acids retained stabilizing effect despite the relatively low pH favoring protonated forms of the chelators.

In yet further preferred aspects, while antioxidants are generally believed to improve stability of isoproterenol, the inventors unexpectedly discovered that isoproterenol in the formulations as presented herein did not benefit from a variety of antioxidants when such antioxidants were part of the formulation as is described in more detail below. However, where non-contact antioxidants (i.e., oxygen (O2) scavengers not in direct contact with the formulation) were employed, desirable storage stability was observed. Therefore, it is generally preferred that the formulations as presented herein are packaged in a container that is disposed in a secondary container, and that an oxygen scavenger is disposed in the space between the container and the second container. For example, suitable oxygen scavenger include iron-based and metal free oxygen scavengers. Moreover, it should be noted that isoproterenol formulations were stable as described in more detail below, especially where deoxygenated solvents (e.g., typically water and/or buffer) were employed. Deoxygenation (i.e., reduction of molecular dissolved oxygen) can be achieved in numerous manners, including sparging with inert gases (e.g., helium, various freons, argon, xenon), agitation under vacuum, and/or using enzymatic systems that deplete a solution of dissolved oxygen (see e.g., U.S. Pat. No. 9,187,779). Of course, where a head space above the formulation is present in the container, it is contemplated that the head space can be flushed with an inert gas such as nitrogen or helium. As noted above, ingress of molecular oxygen into the formulation can also be reduced by co-packaging a container with the formulation in a secondary container that includes an oxygen scavenger, and especially a metal-free oxygen scavenger (e.g., GLS100, Ageless®, Pharmakeep®, all commercially available from Mitsubishi Gas Chemical America).

With respect to suitable tonicity agents it is generally preferred that the tonicity agent will be non-reactive with the isoproterenol, and various carbohydrates and sugar alcohols are therefore less preferred. In contrast, inorganic salts are preferred, and it is contemplated that such salt will be a pharmaceutically acceptable salt that can be used to increase tonicity. For example, pharmaceutically acceptable salts especially include NaCl, at a concentration of at least 0.6 wt %, or at least 0.7 wt %, or at least 0.8 wt %, or at least 0.9 wt %. For example, suitable salt concentrations are between 0.6 wt % and 1.2 wt %. The amount of tonicity adjusting agent used can be adjusted to obtain osmolality of the formulations in the range of 260 to 340 mOsm/kg. An osmometer can be used to check and adjust the amount of tonicity adjusting agent to be added to obtain the desired osmolality. In still further contemplated aspects, and particularly where the composition is filter sterilized, it is contemplated that the tonicity agent may be a carbohydrate, including dextrose or mannitol.

With respect to the sterilization of contemplated formulations it should be appreciated that contemplated formulations may be sterilized using all known manners of sterilization, including filtration through 0.22 micron (or other suitably sized) filters, heat sterilization, autoclaving, radiation (e.g., gamma, electron beam, microwave), and gas sterilization (e.g., ethylene oxide). However, it is especially preferred that the formulations presented herein are sterilized by autoclaving (especially where a chelator is present) or sterile filtration. As is described in more detail below, the inventors discovered that the isoproterenol formulations presented herein were heat stable and did not undergo significant isomerization, even under conditions of sterilization (exposure to high-pressure saturated steam) at 121° C. for at least 5, or at least 10, or at least 15 minutes, or at least 30 minutes.

Based on the anticipated heat stability, the formulations contemplated herein can also be filtered through a 0.22 micron filter, and filled in to a polyethylene, polypropylene or low-density polyethylene containers in a blow-fill-seal (BFS) process. BFS is a form of advanced aseptic manufacturing wherein the container is formed, filled, and sealed in one continuous, automated system not requiring human intervention. The process begins with the extrusion of plastic granules in the form of a hot hollow pipe of molten plastic called a parison. The next step is the blow molding of the container with an open top through which the container is filled, all while the plastic remains hot and in a molten state. Once filled, the container is hermetically sealed and cooled. The blow-fill seal process can take several seconds, and contemplated ready-to-inject compositions advantageously are formulated to withstand the temperature and pressure requirements without substantial degradation of isoproterenol (e.g., less than 5 wt %, less than 3 wt %, less than 2 wt %, less than 1 wt % degradation).

Once the isoproterenol formulations are filled in large volume polymeric, semi-permeable infusion containers (e.g., BFS container or flexible IV bags), the containers can optionally be layered or covered with a secondary packaging system including an aluminum pouch or other oxygen scavenger. For example, the BFS containers can further be sealed in an oxygen and moisture barrier blister packaging. The blister packaging can comprise one or more layers, and the one or more layers can include aluminum foil or other oxygen absorber having an Oxygen Transmission Rate (OTR) between 0.0005 to 5.00 cc/100 in$^2$/24 hrs. Additionally or alternatively, one or more oxygen absorbers (metal or metal free, organic material) can be incorporated into any portion of the BFS container, the secondary packaging system, or between the two (e.g., between the BFS container and the multi-layer packaging) such that the oxygen absorber removes at least a portion of oxygen from the air surrounding said oxygen-sensitive drug. A beneficial feature of the oxygen absorber is the absorbance and removal of oxygen present in the primary packaging and in the liquid drug itself. Notably, it was found that the oxygen absorber also removed residual headspace oxygen in the primary packaging and also dissolved oxygen in the liquid over time, thereby further improving stability of isoproterenol.

Suitable packaging volumes include all volumes that are appropriate for direct administration to an individual. For example, contemplated formulations may be packaged at a volume of between 10-25 mL, or between 25-75 mL, or between 75 and 150 mL, or between 150 mL and 250 mL, or even more. Therefore, exemplary formulations may be packaged in a volume of 50 mL, 100 mL, 150 mL, or 250 mL.

Contemplated uses of the compositions presented herein are all known uses in which isoproterenol is administered to a subject in need thereof. Thus, suitable uses include treatment of mild or transient episodes of heart block that do not require electric shock or pacemaker therapy, serious episodes of heart block and Adams-Stokes attacks (except when caused by ventricular tachycardia or fibrillation), and use in cardiac arrest until electric shock or pacemaker therapy is available. Additionally, contemplated compositions may also be used for treatment of bronchospasm occurring during anesthesia. In still further contemplated uses, the compositions presented herein are employed as an adjunct to fluid and electrolyte replacement therapy. In yet further uses, contemplated compositions and can be administered in the treatment of hypovolemic and septic shock, low cardiac output (hypoperfusion) states, congestive heart failure, and cardiogenic shock. In such uses, it should be especially noted that the compositions presented herein are administered to the subject in need thereof without prior dilution.

Examples

The following examples are intended as representative embodiments of the inventive subject matter and should not be construed as limiting the scope of the invention. Unless noted otherwise, exemplary formulations for a 4 mcg/mL isoproterenol hydrochloride composition were prepared and filled into polypropylene IV bags as primary container. All tested formulations were subjected to accelerated storage conditions of 40° C., 75% RH, 60° C., and/or 80° C. Solutions stored for 2-3 weeks at 60° C. and 5-7 days at 80° C. were estimated to be reflective of storage conditions in room temperature for approximately 2 years. Moreover, it should be noted that unless indicated otherwise, isoproterenol hydrochloride was a racemic mixture of both stereoisomers. Unless indicated otherwise, all percentages are weight percentages (wt %) or expressed as weight by volume (w/v).

Initial pH evaluation included tests at pH 3.0, 3.5, 4.0, 4.5, 5.0 and pH 5.5, and exemplary compositions for the tested formulations are shown in Table 2. The solutions were dispensed in molded type 1 borosilicate glass vials, capped with rubber stopper and crimped with an aluminum seal. Storage was at 40° C./75% RH for up to 9 days.

TABLE 2

| | Quantity per mL | | | | | |
| --- | --- | --- | --- | --- | --- | --- |
| Ingredient | Lot # 12945-1 | Lot # 12945-2 | Lot # 12945-3 | Lot # 12945-4 | Lot # 12945-5 | Lot # 12945-6 |
| Isoproterenol HCl | 4 mcg | 4 mcg | 4 mcg | 4 mcg | 4 mcg | 4 mcg |
| 10N NaOH/HCl | q.s. pH 3.0 | q.s. pH 3.5 | q.s. pH 4.0 | q.s. pH 4.5 | q.s. pH 5.0 | q.s. pH 5.5 |
| Water for Injection | q.s. 1 mL | q.s. 1 mL | q.s. 1 mL | q.s. 1 mL | q.s. 1 mL | q.s. 1 mL |

Table 3 and Table 4 show experimental data using the formulations of Table 2. CCS denotes 'clear colorless solution', NR denotes 'Not Reported (<0.1%)', and NT denotes 'Not Tested'. As can be taken from the results, the stability of isoproterenol hydrochloride was optimal at pH 3.0, 3.5 and 4.0, and pH 4.5 appeared to be the edge of failure. Solutions at pH 5.0 and 5.5 were heavily degraded after 3 days at 40° C./75% RH. As contemplated formulations are intravenously administered, pH is a significant consideration aside from stability (especially in view of risk of vein irritation and hemocompatibility). In view of the stability results, pH 4.0 was chosen for further evaluation.

TABLE 3

| | 40° C./75% RH | | | | | | | | | | | |
|---|---|---|---|---|---|---|---|---|---|---|---|---|
| | pH 3.0 (Lot # 12945-1) | | | | pH 3.5 (Lot # 12945-2) | | | | pH 4.0 (Lot # 12945-3) | | | |
| | Time point | | | | | | | | | | | |
| | Initial | 1 Day | 5 Day | 9 Day | Initial | 1 Day | 5 Day | 9 Day | Initial | 1 Day | 5 Day | 9 Day |
| Appearance | CCS | CCS | CCS | CCS | CCS | CCS | CCS | CCS | CCS | CCS | CCS | CCS |
| pH | 3.01 | 3.04 | 2.97 | 2.91 | 3.52 | 3.57 | 3.46 | 3.45 | 4.01 | 4.02 | 3.96 | 3.94 |
| Assay (%) | 97.8 | 95.8 | 86.3 | 79.7 | 101.6 | 99.8 | 91.0 | 84.2 | 102.3 | 100.7 | 90.5 | 81.4 |

TABLE 4

| | 40° C./75% RH | | | | | | | | | | | |
|---|---|---|---|---|---|---|---|---|---|---|---|---|
| | pH 4.5 (Lot # 12945-4) | | | | pH 5.0 (Lot # 12945-5) | | | | pH 5.5 (Lot # 12945-6) | | | |
| | Time point | | | | | | | | | | | |
| | Initial | 1 Day | 5 Day | 9 Day | Initial | 1 Day | 5 Day | 9 Day | Initial | 1 Day | 5 Day | 9 Day |
| Appearance | CCS | CCS | CCS | CCS | CCS | CCS | Clear pink solution | Clear pink solution | CCS | Clear pink solution | Clear pink solution | Clear pink solution |
| pH | 4.50 | 4.54 | 4.49 | 4.53 | 5.05 | 5.01 | 4.83 | 4.82 | 5.50 | 5.10 | 5.33 | 5.21 |
| Assay (%) | 101.3 | 97.0 | 70.9 | 58.4 | 101.6 | 88.5 | 48.4 | 29.6 | 92.3 | 43.8 | 19.0 | 14.9 |

After the initial determination that pH 4.0 would provide suitable stability that is closer to a physiological pH, the inventors then tested suitable buffer system and concentrations. After a series of initial experiments (data not shown), acetate, tartrate, and glutamate buffer systems were evaluated at 5 mM concentration, and Table 5 shows exemplary compositions for the isoproterenol solutions.

TABLE 5

| | Quantity in mL | | |
|---|---|---|---|
| Ingredient | Lot # 13085 | Lot # 13086 | Lot # 13087 |
| Isoproterenol hydrochloride | 4 mcg | 4 mcg | 4 mcg |
| Buffer  Glacial acetic acid | 0.144 mg | — | — |
| L-tartaric acid | — | 750.4 mcg | — |
| L-glutamic acid | — | — | 735.6 mcg |
| 10N NaOH/6N HCl | q.s. pH 4.0 | q.s. pH 4.0 | q.s. pH 4.0 |
| Water for Injection | q.s. 1 mL | q.s. 1 mL | q.s. 1 mL |

The experimental data for the specific buffer systems are shown in Tables 6-8 illustrating the optimal stability of isoproterenol hydrochloride in tartrate relative to acetate and glutamate buffer systems. Notably, despite the very low buffer concentration, the tartrate buffer system maintained the chemical stability (reflective on consistent assay values) and the pH of the isoproterenol hydrochloride solution. In contrast, a gradual drop in assay values was found for solutions comprising acetate buffer, and a gradual pH drift was observed for the glutamate buffer system. Out of the three buffer systems, the tartrate buffer system yielded the lowest total impurity values after 3-week storage at 60° C. and 80° C. Therefore, tartrate buffer was selected for further evaluations.

TABLE 6

| | | Lot # 13085 | | | | | | | |
|---|---|---|---|---|---|---|---|---|---|
| | | | 60° C. | | | | 80° C. | | |
| Time point | | Initial | 1 Week | 2 Week | 3 Week | 2 Day | 5 Day | 1 Week | 2 Week |
| Appearance | | CCS | CCS | CCS | CCS | CCS | CCS | CCS | CCS |
| pH | | 4.07 | 4.05 | 4.05 | 4.07 | 4.07 | 4.04 | 4.06 | 4.07 |
| Dissolved Oxygen (ppm) | | 1.14 | 1.26 | 1.34 | 1.07 | 1.31 | 1.03 | 1.06 | 1.17 |
| Assay (%) | | 98.7 | 98.1 | 97.4 | 96.9 | 97.5 | 96.6 | 95.4 | 93.0 |
| Related substance (%) | Imp-A | NR | NR | NR | NR | NR | 0.11 | 0.11 | 0.16 |
| | Unknown (RRT) | NR (1.31) 0.21 (2.95) | NR (1.31) 0.56 (1.42) 0.35 (1.55) 2.10 (2.47) | NR (1.20) NR (1.31) 0.65 (1.42) 0.54 (1.55) | NR (1.20) NR (1.31) 1.15 (1.42) 0.97 (1.55) | NR (1.31) 0.31 (1.42) 0.41 (1.55) 2.05 (2.47) | NR (1.20) NR (1.31) 0.63 (1.42) 0.87 (1.55) | NR (1.20) NR (1.31) 1.02 (1.42) 1.42 (1.55) | NR (1.20) NR (1.31) 1.13 (1.42) 1.52 (1.55) |

TABLE 6-continued

| | Lot # 13085 | | | | | | | |
|---|---|---|---|---|---|---|---|---|
| | 60° C. | | | | 80° C. | | | |
| Time point | Initial | 1 Week | 2 Week | 3 Week | 2 Day | 5 Day | 1 Week | 2 Week |
| | | 0.28 (2.95) | 1.77 (2.47) | 2.54 (2.47) | 0.44 (2.95) | 3.85 (2.47) | 4.56 (2.47) | 0.13 (1.60) |
| | | | 0.17 (2.95) | | | 0.74 (2.95) | 0.78 (2.95) | 5.48 (2.47) |
| | | | | | | | | 0.63 (2.95) |
| Total Impurity (%) | 0.21 | 3.29 | 3.14 | 4.66 | 3.22 | 6.20 | 7.89 | 9.06 |

TABLE 7

| | | Lot # 13086 | | | | | | | |
|---|---|---|---|---|---|---|---|---|---|
| | | 60° C. | | | | 80° C. | | | |
| Time point | | Initial | 1 Week | 2 Week | 3 Week | 2 Day | 5 Day | 1 Week | 2 Week |
| Appearance | | CCS | CCS | CCS | CCS | CCS | CCS | CCS | CCS |
| pH | | 4.05 | 4.04 | 4.06 | 4.04 | 4.02 | 4.05 | 4.06 | 4.04 |
| Dissolved Oxygen (ppm) | | 1.42 | 1.05 | 1.18 | 1.18 | 1.33 | 1.04 | 1.15 | 1.22 |
| Assay (%) | | 99.6 | 100.4 | 99.3 | 100.4 | 100.0 | 99.9 | 99.1 | 97.6 |
| Related | Imp-A | NR | NR | NR | NR | NR | NR | NR | NR |
| substance | Unknown | NR (1.31) | NR (1.31) | 0.10 (1.31) | NR (1.31) | NR (1.31) | NR (1.31) | 0.12 (1.31) | NR (1.20) |
| (%) | (RRT) | | 0.31 (1.42) | 0.43 (1.42) | 0.52 (1.42) | 0.26 (1.42) | 0.51 (1.42) | 0.70 (1.42) | 0.18 (1.31) |
| | | | NR (1.55) | 0.17 (1.55) | 0.22 (1.55) | 0.13 (1.55) | 0.30 (1.55) | 0.38 (1.55) | 0.82 (1.42) |
| | | | NR 2.95) | 0.29 (2.47) | NR (2.47) | 0.16 (2.95) | 0.20 (2.95) | 0.22 (2.95) | 0.43 (1.55) |
| | | | | | | | | | 0.50 (2.47) |
| | | | | | | | | | 0.14 (2.95) |
| Total Impurity (%) | | NR | 0.31 | 0.99 | 0.75 | 0.55 | 1.01 | 1.41 | 2.08 |

TABLE 8

| | | Lot # 13087 | | | | | | | |
|---|---|---|---|---|---|---|---|---|---|
| | | 60° C. | | | | 80° C. | | | |
| Time point | | Initial | 1 Week | 2 Week | 3 Week | 2 Day | 5 Day | 1 Week | 2 Week |
| Appearance | | CCS | CCS | CCS | CCS | CCS | CCS | CCS | CCS |
| pH | | 4.04 | 3.99 | 3.89 | 3.73 | 3.79 | 3.40 | 3.37 | 3.24 |
| Dissolved Oxygen (ppm) | | 1.20 | 1.16 | 1.12 | 1.10 | 1.30 | 1.16 | 1.18 | 1.13 |
| Assay (%) | | 99.1 | 99.4 | 98.8 | 99.5 | 99.3 | 98.9 | 99.1 | 97.3 |
| Related | Imp-A | NR | NR | NR | NR | NR | NR | NR | NR |
| substance | Unknown | NR (1.31) | NR (1.31) | NR (1.31) | NR (1.31) | NR (1.31) | NR (1.31) | NR (1.31) | NR (1.31) |
| (%) | (RRT) | 0.15 (1.85) | 0.27 (1.42) | 0.15 (1.20) | 0.51 (1.42) | 0.28 (1.42) | 0.69 (1.42) | 0.48 (1.42) | 0.90 (1.42) |
| | | | NR (1.55) | 0.33 (1.42) | 0.26 (1.55) | 0.17 (1.55) | 0.43 (1.55) | 0.29 (1.55) | 0.48 (1.55) |
| | | | 0.10 (1.85) | 0.15 (1.55) | 0.31 (2.47) | NR (1.85) | NR (1.85) | NR (1.85) | 0.67 (2.47) |
| | | | 0.32 (2.95) | NR (1.85) | | NR (2.47) | 0.12 (2.47) | 0.31 (2.95) | 0.24 (2.95) |
| | | | | 0.41 (2.47) | | NR (2.95) | 0.25 (2.95) | | |
| | | | | 0.14 (2.95) | | | | | |
| Total Impurity (%) | | 0.15 | 0.68 | 1.18 | 1.08 | 0.45 | 1.48 | 1.09 | 2.30 |

Based on the above results, the inventors further investigated additional buffer concentrations for isoproterenol hydrochloride solutions at pH 4.0. Concentrations of 5 mM, 2 mM, 1 mM, 0.5 mM, 0.25 mM and 0 mM (control) were assessed and exemplary formulation compositions are shown in Table 9.

TABLE 9

| | Quantity in mL | | | | | |
|---|---|---|---|---|---|---|
| Ingredient | Lot # 13347-2 | Lot # 13347-3 | Lot # 13347-4 | Lot # 13396-1 | Lot # 13396-2 | Lot # 13347-5 |
| Isoproterenol hydrochloride | 4 mcg | 4 mcg | 4 mcg | 4 mcg | 4 mcg | 4 mcg |

TABLE 9-continued

| | | Quantity in mL | | | | | |
|---|---|---|---|---|---|---|---|
| Ingredient | | Lot # 13347-2 | Lot # 13347-3 | Lot # 13347-4 | Lot # 13396-1 | Lot # 13396-2 | Lot # 13347-5 |
| Buffer | Concentration | 5 mM | 2 mM | 1 mM | 0.5 mM | 0.25 mM | 0 mM |
| | L-tartaric acid | 750.0 mcg | 300.0 mcg | 150.0 mcg | 75.0 mcg | 37.5 mcg | — |
| | 10N NaOH/6N HCl | q.s. pH 4.0 | q.s. pH 4.0 | q.s. pH 4.0 | q.s. pH 4.0 | q.s. pH 4.0 | q.s. pH 4.0 |
| | Water for Injection | q.s. 1 mL | q.s. 1 mL | q.s. 1 mL | q.s. 1 mL | q.s. 1 mL | q.s. 1 mL |

The results for these experiments are shown in Tables 10-11. As can be readily seen from the data, the positive effect of all tested tartrate buffer concentrations on the stability of isoproterenol hydrochloride solution is apparent, even at very low buffer concentrations. In contrast, a drop in assay value and increased impurity levels were observed for the control (no buffer, but pH adjusted to 4.0). The pH was retained at 4.0 on all tested conditions therefore all tartrate concentrations were poised suitable to maintain optimal pH. While assay values were comparable in all buffered solutions, a slight increase in impurity level was observed as tartrate concentration decreased. This suggest that aside retaining the pH of the solution, tartaric acid may impart stability through another mechanism. Nonetheless, even the lowest tested tartrate concentration of 0.25 mM has significantly lower impurity levels than the unbuffered control. Where it is desired that total quantities of administered tartrate be limited, concentrations of 1 mM tartrate buffer and below can therefore be employed. For example, for a 100 mL fill volume of contemplated formulations, 1 mM and 0.25 mM tartrate buffer will result in a total of 15 mg and 3.75 mg tartaric acid, respectively. Therefore, buffer concentrations of 1 mM and 0.25 mM were used for further testing.

TABLE 10

| | | Condition | | | | | |
|---|---|---|---|---|---|---|---|
| | | 5 mM Tartrate buffer (Lot # 13347-2) | | | | 2 mM Tartrate buffer (Lot # 13347-3) | |
| Time point | | Initial | 1 Week | 2 Week | 3 Week | Initial | 1 Week |
| Appearance | | CCS | CCS | CCS | CCS | CCS | CCS |
| pH | | 4.05 | 4.06 | 4.08 | 4.06 | 4.04 | 4.05 |
| Dissolved Oxygen (ppm) | | 1.44 | 1.13 | 1.13 | 1.21 | 1.46 | 1.11 |
| Assay (%) | | 97.6 | 98.2 | 98.8 | 98.6 | 97.7 | 98.3 |
| Related | Imp-A | NR | NR | NR | NR | NR | NR |
| substance (%) | Unknown (RRT) | NR (1.31) | NR (1.31) 0.17 (1.42) 0.20 (2.47) | NR (1.31) 0.37 (1.42) 0.15 (1.55) NR (1.55) | NR (1.31) 0.42 (1.42) 0.17 (1.55) 0.12 (2.47) 0.19 (2.95) | NR (1.31) | NR (1.31) 0.17 (1.42) 0.11 (1.55) |
| Total Impurity (%) | | NR | 0.38 | 0.96 | 0.91 | NR | 0.27 |

| | | Condition | | | | | |
|---|---|---|---|---|---|---|---|
| | | 2 mM Tartrate buffer (Lot # 13347-3) | | 1 mM Tartrate buffer (Lot # 13347-4) | | | |
| Time point | | 2 Week | 3 Week | Initial | 1 Week | 2 Week | 3 Week |
| Appearance | | CCS | CCS | CCS | CCS | CCS | CCS |
| pH | | 4.03 | 4.05 | 4.09 | 4.09 | 4.09 | 4.09 |
| Dissolved Oxygen (ppm) | | 1.13 | 1.11 | 1.36 | 1.01 | 1.26 | 1.08 |
| Assay (%) | | 98.9 | 98.5 | 97.9 | 98.1 | 99.2 | 98.9 |
| Related | Imp-A | NR | NR | NR | NR | NR | NR |
| substance (%) | Unknown (RRT) | NR (1.31) 0.37 (1.42) 0.24 (1.55) 0.12 (2.47) 0.18 (2.95) | NR (1.31) 0.33 (1.42) 0.19 (1.55) 0.13 (2.47) 0.21 (2.95) | NR (1.31) | NR (1.31) 0.11 (1.42) NR (1.55) 0.33 (2.47) | NR (1.31) 0.19 (1.42) 0.15 (1.55) NR (2.13) 0.49 (2.47) | NR (1.31) 0.25 (1.42) 0.19 (1.55) 0.36 (2.47) 0.27 (2.95) 0.25 (2.95) |
| Total Impurity (%) | | 0.91 | 0.86 | NR | 0.44 | 1.08 | 1.06 |

TABLE 11

| | Condition | | | | | |
|---|---|---|---|---|---|---|
| | 0.5 mM Tartrate buffer (Lot # 13396-1) | | | | 0.25 mM Tartrate buffer (Lot # 13396-2) | |
| Time point | Initial | 1 Week | 2 Week | 3 Week | Initial | 1 Week |
| Appearance | CCS | CCS | CCS | CCS | CCS | CCS |
| pH | 4.07 | 4.05 | 4.05 | 4.04 | 4.05 | 4.08 |
| Dissolved Oxygen (ppm) | 1.15 | 1.03 | 1.23 | 1.11 | 1.44 | 1.15 |
| Assay (%) | 99.0 | 98.3 | 97.9 | 98.4 | 98.8 | 97.8 |
| Related substance (%) Imp-A | NR | NR | NR | NR | NR | NR |
| Unknown (RRT) | NR (1.31) | NR (1.31) | NR (1.31) | NR (1.31) | NR (1.31) | NR (1.31) |
| | NR (2.95) | NR (1.42) | 0.23 (1.42) | 0.27 (1.42) | 0.14 (2.95) | NR (1.42) |
| | | NR (1.55) | 0.20 (1.55) | 0.24 (1.55) | | NR (1.55) |
| | | 0.35 (2.47) | NR (2.13) | 0.12 (2.13) | | 0.87 (2.47) |
| | | 0.26 (2.95) | 0.60 (2.47) | 0.86 (2.47) | | 0.25 (2.95) |
| | | | 0.23 (2.95) | 0.33 (2.95) | | |
| Total Impurity (%) | NR | 0.61 | 1.26 | 1.81 | 0.14 | 1.12 |

| | Condition | | | | | |
|---|---|---|---|---|---|---|
| | 0.25 mM Tartrate buffer (Lot # 13396-2) | | 0 mM Tartrate buffer-control (Lot # 13396-5) | | | |
| Time point | 2 Week | 3 Week | Initial | 1 Week | 2 Week | 3 Week |
| Appearance | CCS | CCS | CCS | CCS | CCS | CCS |
| pH | 4.02 | 4.04 | 4.05 | 4.09 | 4.09 | 4.08 |
| Dissolved Oxygen (ppm) | 1.20 | 1.01 | 1.45 | 0.99 | 1.36 | 1.23 |
| Assay (%) | 97.6 | 97.8 | 97.4 | 96.2 | 94.9 | 95.5 |
| Related substance (%) Imp-A | NR | NR | NR | 0.19 | 0.37 | 0.24 |
| Unknown (RRT) | NR (1.31) | NR (1.20) | NR (1.31) | NR (1.31) | NR (1.31) | NR (0.39) |
| | 0.18 (1.42) | NR (1.31) | 0.51 (2.95) | 0.11 (1.42) | 0.26 (1.20) | NR (1.31) |
| | 0.14 (1.55) | 0.22 (1.42) | | 0.13 (1.55) | 0.39 (1.42) | 0.19 (1.20) |
| | 1.26 (2.47) | 0.22 (1.55) | | 2.59 (2.47) | 0.41 (1.55) | 0.37 (1.42) |
| | 0.16 (2.95) | 0.11 (2.13) | | | NR (1.60) | 0.38 (1.55) |
| | | 1.38 (2.47) | | | 4.38 (2.47) | 2.74 (2.47) |
| | | 0.28 (2.95) | | | 0.29 (2.95) | 0.28 (2.95) |
| Total Impurity (%) | 1.74 | 2.22 | 0.51 | 3.01 | 6.10 | 4.20 |

In still further experiments, the inventors investigated whether addition of a chelator would have an influence on stability of isoproterenol. To that end, the effect of a metal chelator on isoproterenol hydrochloride solution comprising of either 0.25 mM or 1 mM tartrate buffer at pH 4.0 was explored. The presence of divalent metal cations such as iron and copper may facilitate oxidative degradation of isoproterenol either via Fenton reaction or redox reaction. Metal-catalyzed oxidation of isoproterenol could potentially be controlled by sequestering metal cations using chelators such as edetate disodium dihydrate (EDTA). Therefore, EDTA at a concentration of 1.0 mcg/mL, 5.0 mcg/mL and 10.0 mcg/mL were evaluated, and the compositions for these solutions are presented in Tables 12-13.

TABLE 12

| | Quantity in mL | | | | |
|---|---|---|---|---|---|
| Ingredient | Lot # 13516-1 | Lot # 13516-2 | Lot # 13516-3 | Lot # 13516-4 | Lot # 13516-5 |
| Isoproterenol hydrochloride | 4 mcg | 4 mcg | 4 mcg | 4 mcg | 4 mcg |
| L-tartaric acid | 37.5 mcg | 37.5 mcg | 37.5 mcg | 37.5 mcg | 37.5 mcg |
| Edetate disodium dihydrate (EDTA) | — | — | 1.0 mcg | 5.0 mcg | 10.0 mcg |
| 10N Sodium hydroxide/6N Hydrochloric acid | q.s. pH 4.0 | q.s. pH 4.0 | q.s. pH 4.0 | q.s. pH 4.0 | q.s. pH 4.0 |
| Water for Injection | q.s. 1 mL | q.s. 1 mL | q.s. 1 mL | q.s. 1 mL | q.s. 1 mL |

TABLE 13

| Ingredient | Quantity in mL | | |
|---|---|---|---|
| | Lot # 13517-2 | Lot # 13517-3 | Lot # 13517-4 |
| Isoproterenol hydrochloride | 4 mcg | 4 mcg | 4 mcg |
| L-tartaric acid | 150.0 mcg | 150.0 mcg | 150.0 mcg |
| Edetate disodium dihydrate (EDTA) | 1.0 mcg | 5.0 mcg | 10.0 mcg |
| 10N Sodium hydroxide/ 6N Hydrochloric acid | q.s. pH 4.0 | q.s. pH 4.0 | q.s. pH 4.0 |
| Water for Injection | q.s. 1 mL | q.s. 1 mL | q.s. 1 mL |

In addition, the inventors also performed an initial evaluation on the effect of autoclaving on isoproterenol stability. Test batches dispensed in polypropylene bags were autoclaved (steam sterilized) at 121° C. with an exposure time of 15 minutes following an air over-pressure (AOP) cycle. The cooled bags were then packaged (vacuum-sealed) in an aluminum overwrap secondary container containing oxygen scavenger.

Significant degradation was found in autoclaved solutions of control (Table 14) However, addition of EDTA at all tested concentrations to isoproterenol hydrochloride solution unexpectedly imparted stability upon terminal sterilization as can be seen from the results in Tables 15-16. Notably, 5 mcg/mL EDTA appeared optimal in both 0.25 mM and 1 mM tartrate buffer with respect to isoproterenol stabilization. While the assay values appeared comparable, the impurity profiles and total impurities suggest that 5 mcg/mL concentration was lower as compared to 1 mcg/mL and 10 mcg/mL EDTA concentrations (5 mcg/ml>1 mcg/mL>10 mcg/mL). No distinct differentiation on the solution stability could be detected between 0.25 mM and 1 mM tartrate buffer in the presence of EDTA.

TABLE 14

| | | 60° C. | | | | | | |
|---|---|---|---|---|---|---|---|---|
| | | control, no metal chelator, not autoclaved (Lot # 13516-1) | | | | control, no metal chelator, autoclaved (Lot # 13516-2) | | |
| Time point | | Initial | 1 Week | 2 Week | 3 Week | Initial | 1 Week | 2 Week |
| Appearance | | CCS | CCS | CCS | CCS | clear faint orange solution | clear faint orange solution | clear faint orange solution |
| pH | | 4.02 | 4.08 | 4.04 | 4.05 | 4.08 | 4.02 | 4.09 |
| Dissolved Oxygen (ppm) | | 1.61 | 1.16 | 1.23 | 1.17 | 2.27 | 1.25 | 1.22 |
| Assay (%) | | 98.7 | 98.1 | 96.9 | 94.1 | 73.5 | 69.8 | 70.7 |
| Related substance (%) | Imp-A | NR | 0.12 | 0.11 | 0.26 | 1.54 | 1.36 | 0.96 |
| | Unknown (RRT) | NR (1.31) | NR (1.31) | NR (1.31) | NR (1.31) | 0.76 (1.1) | 0.23 (0.42) | 2.03 (1.20) |
| | | 0.15 (2.95) | 0.13 (1.42) | 0.28 (1.42) | 0.35 (1.20) | 0.10 (1.31) | 0.19 (0.46) | 0.96 (1.42) |
| | | | 0.12 (1.55) | 0.23 (1.55) | 0.79 (1.42) | 0.11 (1.55) | 0.55 (0.70) | 0.77 (1.55) |
| | | | 0.11 (1.71) | 2.16 (2.47) | 0.65 (1.55) | 0.21 (1.71) | 1.50 (1.20) | 0.24 (1.71) |
| | | | 0.17 (2.42) | 0.32 (2.95) | 0.10 (1.71) | 0.24 (2.13) | 0.54 (1.42) | 0.29 (2.20) |
| | | | 1.39 (2.47) | | 4.34 (2.47) | 4.03 (2.47) | 0.54 (1.55) | 5.93 (2.47) |
| | | | 0.37 (2.95) | | 0.27 (2.95) | 4.61 (2.70) | 0.14 (1.56) | 3.62 (2.70) |
| | | | | | | 0.21 (2.95) | 0.11 (1.58) | |
| | | | | | | | 0.20 (1.71) | |
| | | | | | | | 0.10 (1.78) | |
| | | | | | | | 0.10 (2.00) | |
| | | | | | | | 0.19 (2.16) | |
| | | | | | | | 0.12 (2.20) | |
| | | | | | | | 0.13 (2.26) | |
| | | | | | | | 0.33 (2.42) | |
| | | | | | | | 4.80 (2.47) | |
| | | | | | | | 4.61 (2.70) | |
| | | | | | | | 0.27 (2.80) | |
| | | | | | | | 0.13 (2.84) | |
| | | | | | | | 0.55 (2.92) | |
| | | | | | | | 0.19 (2.94) | |
| | | | | | | | 0.24 (2.95) | |
| | | | | | | | 0.26 (3.11) | |
| Total Impurity (%) | | 0.15 | 2.40 | 3.10 | 6.77 | 11.81 | 17.37 | 14.79 |

TABLE 15

| | 60° C. | | | | | |
|---|---|---|---|---|---|---|
| | 1 mcg/mL EDTA, autoclaved (Lot # 13516-3) | | | | 5 mcg/m EDTA, autoclaved (Lot # 13516-4) | |
| Time point | Initial | 1 Week | 2 Week | 3 Week | Initial | 1 Week |
| Appearance | CCS | CCS | CCS | CCS | CCS | CCS |
| pH | 4.14 | 4.12 | 4.13 | 4.13 | 4.09 | 4.08 |
| Dissolved Oxygen (ppm) | 2.19 | 1.21 | 1.01 | 1.09 | 2.32 | 1.33 |

TABLE 15-continued

| | | | | | | | |
|---|---|---|---|---|---|---|---|
| Assay (%) | | 98.9 | 99.4 | 98.3 | 98.0 | 98.9 | 99.4 |
| Related | Imp-A | NR | NR | NR | NR | NR | NR |
| substance | Unknown | NR (1.31) | NR (1.31) | NR (1.31) | NR (1.31) | NR (1.31) | NR (1.31) |
| % | (RRT) | 0.74 (2.95) | NR (1.42) | 0.17 (1.42) | 0.24 (1.42) | NR (1.71) | NR (1.42) |
| | | | 0.11 (1.55) | 0.17 (1.55) | 0.25 (1.55) | 0.55 (2.95) | 0.11 (1.55) |
| | | | 0.66 (2.95) | 0.65 (2.95) | NR (2.47) | | NR (1.71) |
| | | | | | 0.60 (2.95) | | 0.54 (2.95) |
| Total Impurity (%) | | 0.74 | 0.77 | 1.00 | 1.10 | 0.55 | 0.65 |

| | 60° C. | | | | | |
|---|---|---|---|---|---|---|
| | 5 mcg/m EDTA, autoclaved (Lot # 13516-4) | | 10 mcg/mL, autoclaved (Lot # 13516-5) | | | |
| Time point | 2 Week | 3 Week | Initial | 1 Week | 2 Week | 3 Week |
| Appearance | CCS | CCS | CCS | CCS | CCS | CCS |
| pH | 4.06 | 4.08 | 4.06 | 4.09 | 4.09 | 4.07 |
| Dissolved Oxygen (ppm) | 1.07 | 1.07 | 2.14 | 1.20 | 1.14 | 1.26 |
| Assay (%) | 98.3 | 98.2 | 98.6 | 99.1 | 97.8 | 97.9 |
| Related Imp-A | NR | NR | NR | NR | NR | NR |
| substance Unknown | NR (1.31) | NR (1.31) | NR (1.31) | NR (1.31) | NR (1.31) | NR (1.31) |
| % (RRT) | 0.18 (1.42) | 0.25 (1.42) | NR (1.71) | 0.11 (1.42) | 0.20 (1.42) | 0.29 (1.42) |
| | 0.17 (1.55) | 0.23 (1.55) | 0.73 (2.95) | 0.12 (1.55) | 0.19 (1.55) | 0.27 (1.55) |
| | NR (1.71) | NR (1.71) | | NR (1.71) | NR (1.71) | NR (1.71) |
| | 0.55 (2.95) | NR (2.47) | | 0.79 (2.95) | 0.76 (2.95) | 0.11 (2.47) |
| | | 0.51 (2.95) | | | | 0.75 (2.95) |
| Total Impurity (%) | 0.90 | 0.99 | 0.73 | 1.01 | 1.15 | 1.42 |

TABLE 16

| | 60° C. | | | | | |
|---|---|---|---|---|---|---|
| | 1 mcg/mL EDTA, autoclaved (Lot # 13517-2) | | | | 5 mcg/m EDTA, autoclaved (Lot # 13517-3) | |
| Time point | Initial | 1 Week | 2 Week | 3 Week | Initial | 1 Week |
| Appearance | CCS | CCS | CCS | CCS | CCS | CCS |
| pH | 4.10 | 4.08 | 4.10 | 4.07 | 4.07 | 4.05 |
| Dissolved Oxygen (ppm) | 1.36 | 1.19 | 1.04 | 1.10 | 1.41 | 1.09 |
| Assay (%) | 99.6 | 99.9 | 98.6 | 98.9 | 99.7 | 100.2 |
| Related Imp-A | NR | NR | NR | NR | NR | NR |
| substance Unknown | NR (1.31) | NR (1.31) | NR (1.31) | NR (1.31) | NR (1.31) | NR (1.31) |
| (%) (RRT) | NR (1.55) | 0.15 (1.42) | 0.30 (1.42) | 0.42 (1.42) | NR (1.55) | 0.12 (1.42) |
| | 0.74 (2.95) | 0.15 (1.55) | 0.22 (1.55) | 0.31 (1.55) | NR (1.71) | 0.11 (1.55) |
| | | 0.70 (2.95) | 0.61 (2.95) | 0.56 (2.95) | 0.37 (2.95) | NR (1.71) |
| | | | | | | 0.49 (2.95) |
| Total Impurity (%) | 0.74 | 1.00 | 1.13 | 1.29 | 0.37 | 0.72 |

| | 60° C. | | | | | |
|---|---|---|---|---|---|---|
| | 5 mcg/m EDTA, autoclaved (Lot # 13517-3) | | 10 mcg/mL, autoclaved (Lot # 13517-4) | | | |
| Time point | 2 Week | 3 Week | Initial | 1 Week | 2 Week | 3 Week |
| Appearance | CCS | CCS | CCS | CCS | CCS | CCS |
| pH | 4.01 | 4.01 | 4.06 | 4.08 | 4.04 | 4.03 |
| Dissolved Oxygen (ppm) | 1.04 | 1.41 | 1.49 | 1.21 | 1.09 | 1.16 |
| Assay (%) | 99.0 | 99.1 | 99.4 | 99.9 | 98.5 | 98.6 |
| Related Imp-A | NR | NR | NR | NR | NR | NR |
| substance Unknown | NR (1.31) | NR (1.31) | NR (1.31) | NR (1.31) | NR (1.31) | NR (1.31) |
| (%) (RRT) | 0.20 (1.42) | 0.27 (1.42) | NR (1.55) | 0.15 (1.42) | 0.30 (1.42) | 0.39 (1.42) |
| | 0.15 (1.55) | 0.19 (1.55) | NR (1.71) | 0.13 (1.55) | 0.21 (1.55) | 0.27 (1.55) |
| | NR (1.71) | NR (1.71) | 1.10 (2.95) | NR (1.71) | NR (1.71) | NR (1.71) |
| | 0.55 (2.95) | 0.49 (2.95) | | 0.98 (2.95) | 1.00 (2.95) | 0.22 (2.47) |
| | | | | | | 1.00 (2.95) |
| Total Impurity (%) | 0.90 | 0.95 | 1.10 | 1.25 | 1.52 | 1.87 |

Oxidation of isoproterenol in aqueous solutions is catalyzed by either basic pH, presence of metal cations, or light. Any of these conditions facilitate the activation of molecular oxygen in aqueous solutions to an energetic state in the form of reactive oxygen species and free radicals. Subsequently, isoproterenol readily reacts with reactive oxygen species and free radicals via 1- or 2-electron transfer thereby resulting in its oxidation. In view of the above, the inventors tested mitigation strategies to reduce the risk of light-driven oxidation by using an aluminum overwrap to contain the polypropylene bag. Moreover, dissolved oxygen was sequestered using a non-contact oxygen scavenger placed inside the overwrap.

In selected examples, the effect of oxygen reduction in the form of various antioxidants was evaluated on isoproterenol solution comprising 0.25 mM tartrate buffer with 5 mcg/mL EDTA at pH 4.0 and exemplary formulations are shown in Table 17. Terminally sterilized solutions in polypropylene bags were packaged (vacuum-sealed) in Aluminum overwrap with or without an oxygen scavenger. The non-contact oxygen scavenger was assumed to sequester oxygen from isoproterenol hydrochloride solutions in polypropylene bag though gas permeation/diffusion. Here, pre-activated iron-based ZPT-100 MBC from Mitsubishi Gas Chemical America was used.

The experimental data (Tables 19-21) for formulations with antioxidant at all tested concentrations appeared suboptimal relative to control (Table 18). For instance, two additional unknown impurities, including RRT 1.82 (below the reporting threshold of 0.1%) and RRT 2.93, were observed in solutions containing L-methionine relative to control. Similar observations were made in formulations with sodium metabisulfite and ascorbic acid. Assay values dropped significantly in formulations containing sodium metabisulfite. Analysis for the initial timepoint of the formulation containing 50 mcg/mL sodium metabisulfite already suggested high degradation (assay value of 95.4%) after the terminal sterilization process. Significant numbers of unknown impurities were detected in formulations containing sodium metabisulfite relative to control. Appreciable degradation (based on assay values) relative to the control was also observed for formulations containing ascorbic acid. Based on these data, it is therefore contemplated that the tested antioxidant appeared to react with isoproterenol to form adducts. Interestingly, all formulations containing antioxidants packaged without non-contact oxygen scavenger and stored at 60° C. for 1 week yielded lower assay values and higher total impurity levels relative to those formulations packaged with non-contact oxygen scavenger. This

TABLE 17

| | Quantity per mL | | | | | | |
| --- | --- | --- | --- | --- | --- | --- | --- |
| Ingredient | Lot # 13695 | Lot # 13696-1 | Lot # 13696-2 | Lot # 13697-1 | Lot # 13697-2 | Lot # 13801-1 | Lot # 13801-2 |
| Isoproterenol hydrochloride | 4 mcg | 4 mcg | 4 mcg | 4 mcg | 4 mcg | 4 mcg | 4 mcg |
| L-tartaric acid | 37.5 mcg | 37.5 mcg | 37.5 mcg | 37.5 mcg | 37.5 mcg | 37.5 mcg | 37.5 mcg |
| Edetate disodium dihydrate (EDTA) | 5.0 mcg | 5.0 mcg | 5.0 mcg | 5.0 mcg | 5.0 mcg | 5.0 mcg | 5.0 mcg |
| Antioxidant L-methionine | — | 50.0 mcg | 10.0 mcg | — | — | — | — |
| Sodium metabisulfite | — | — | — | 50.0 mcg | 10.0 mcg | — | — |
| Ascorbic acid | — | — | — | — | — | 50.0 mcg | 10.0 mcg |
| 10N Sodium hydroxide/ 6N Hydrochloric acid | q.s. pH 4.0 | q.s. pH 4.0 | q.s. pH 4.0 | q.s. pH 4.0 | q.s. pH 4.0 | q.s. pH 4.0 | q.s. pH 4.0 |
| Water for Injection | q.s. 1 mL | q.s. 1 mL | q.s. 1 mL | q.s. 1 mL | q.s. 1 mL | q.s. 1 mL | q.s. 1 mL |

The results from these studies are shown in Tables 18-21, indicating the benefit of using a non-contact oxygen scavenger for oxygen control to so achieve significant reduction of oxidative degradation. Total impurity on packaged samples without oxygen scavenger appeared to double relative to those with oxygen scavenger after storage at 60° C. for 1 week. The effect of antioxidant excipients on isoproterenol hydrochloride solution comprising of 0.25 mM tartrate buffer with 5 mcg/mL EDTA at pH 4.0 was also assessed in this study. Oxidation of Isoproterenol may be prevented in the presence of antioxidant poised to quench reactive oxygen species and free radicals in solution. Three potential water-soluble antioxidant candidates were evaluated including L-methionine, sodium metabisulfite and ascorbic acid at either 10 mcg/mL or 50 mcg/mL concentrations. Terminally sterilized investigational Isoproterenol hydrochloride solutions consisting of antioxidants were then packaged (vacuum sealed) in an aluminum overwrap with or without ZPT-100MBC oxygen scavenger. The addition of an effective antioxidant to Isoproterenol hydrochloride solution may render the non-contact oxygen scavenger unnecessary. Conversely, an antioxidant excipient may render oxidative protection during compounding/manufacturing process prior to packaging and the addition of non-contact oxygen scavenger, thereby causing further improvement in Isoproterenol stability.

strongly suggests that the tested antioxidants in the formulations were not able to efficiently suppress oxidative degradation in comparison to having a non-contact oxygen scavenger as a part of the packaging (between the primary and secondary containers).

TABLE 18

| | | 60° C. | | |
| --- | --- | --- | --- | --- |
| | | control with oxygen scavenger (Lot # 13695) | | control without oxygen scavenger (Lot # 13695) |
| Time point | | Initial | 1 Week | Initial | 1 Week |
| Appearance | | CCS | CCS | CCS | CCS |
| pH | | 4.08 | 4.02 | 4.08 | 4.09 |
| Dissolved Oxygen (ppm) | | 1.02 | 1.13 | 7.38 | 6.38 |
| Assay (%) | | 98.9 | 98.0 | 98.7 | 97.5 |
| Related substance (%) | Imp-A | NR | NR | NR | NR |
| | Unknown (RRT) | NR (1.36) 0.49 (3.35) | NR (1.36) NR (1.47) NR (1.62) 0.41 (3.35) | NR (1.36) 0.46 (3.35) | NR (1.36) NR (1.47) NR (1.62) 0.96 (3.35) |
| Total Impurity (%) | | 0.49 | 0.41 | 0.46 | 0.96 |

TABLE 19

| | 60° C. | | | | | | | |
|---|---|---|---|---|---|---|---|---|
| | 10 mcg/mL L-methionine with oxygen scavenger (Lot # 13696-2) | | 10 mcg/mL L-methionine without oxygen scavenger (Lot # 13696-2) | | 50 mcg/mL L-methionine with oxygen scavenger (Lot # 13696-1) | | 50 mcg/mL L-methionine without oxygen scavenger (Lot # 13696-1) | |
| Time point | Initial | 1 Week | Initial | 1 Week | Initial | 1 Week | Initial | 1 Week |
| Appearance | CCS | CCS | CCS | CCS | CCS | CCS | CCS | CCS |
| pH | 4.09 | 4.12 | 4.05 | 4.12 | 4.10 | 4.07 | 4.09 | 4.10 |
| Dissolved Oxygen (ppm) | 1.13 | 1.13 | 7.02 | 6.86 | 1.23 | 1.04 | 6.76 | 6.90 |
| Assay (%) | 97.6 | 96.8 | 97.9 | 96.0 | 97.7 | 96.7 | 97.9 | 95.7 |
| Related substance (%) Imp-A | NR | NR | NR | NR | NR | NR | NR | NR |
| Unknown (RRT) | NR (1.36) | NR (1.36) | NR (1.36) | NR (1.36) | NR (1.36) | NR (1.36) | NR (1.36) | NR (1.36) |
| | NR (1.62) | 0.12 (1.47) | NR (1.62) | 0.11 (1.47) | NR (1.82) | 0.13 (1.47) | NR (1.82) | 0.13 (1.47) |
| | NR (1.82) | 0.12 (1.62) | NR (1.82) | 0.12 (1.62) | 0.76 (3.35) | 0.13 (1.62) | 0.76 (3.35) | 0.12 (1.62) |
| | 0.12 (2.93) | NR (1.82) | 0.57 (3.35) | NR (1.82) | | NR (1.82) | | NR (1.82) |
| | 0.57 (3.35) | 0.53 (3.35) | | NR (2.33) | | 0.72 (3.35) | | 1.41 (3.35) |
| | | | | 1.30 (3.35) | | | | |
| Total Impurity (%) | 0.69 | 0.77 | 0.57 | 1.53 | 0.76 | 0.97 | 0.76 | 1.65 |

TABLE 20

| | 60° C. | | | | | | | |
|---|---|---|---|---|---|---|---|---|
| | 10 mcg/mL sodium metabisulfite with oxygen scavenger (Lot # 13697-2) | | 10 mcg/mL sodium metabisulfite without oxygen scavenger (Lot # 13697-2) | | 50 mcg/mL sodium metabisulfite with oxygen scavenger (Lot # 13697-1) | | 50 mcg/mL sodium metabisulfite without oxygen scavenger (Lot # 13697-1) | |
| Time point | Initial | 1 Week | Initial | 1 Week | Initial | 1 Week | Initial | 1 Week |
| Appearance | CCS | CCS | CCS | CCS | CCS | CCS | CCS | CCS |
| pH | 4.10 | 4.13 | 4.11 | 4.12 | 4.12 | 4.14 | 4.14 | 4.14 |
| Dissolved Oxygen (ppm) | 1.00 | 1.20 | 7.86 | 6.61 | 1.02 | 1.15 | 7.21 | 6.99 |
| Assay (%) | 97.0 | 60.8 | 97.2 | 94.1 | 95.4 | 91.9 | 95.0 | 88.6 |
| Related substance (%) Imp-A | NR | NR | NR | NR | 0.13 | 0.14 | 0.12 | 0.41 |
| Unknown (RRT) | 0.62 (0.73) | 1.09 (0.73) | 0.67 (0.73) | 1.06 (0.73) | 2.59 (0.73) | 5.18 (0.73) | 2.65 (0.73) | 3.63 (0.73) |
| | NR (1.36) | NR (1.36) | NR (1.36) | 0.23 (0.91) | NR (1.36) | NR (1.36) | NR (1.36) | 0.19 (0.91) |
| | NR (1.68) | NR (1.68) | NR (1.68) | NR (1.25) | 0.16 (1.55) | 0.11 (1.55) | NR (1.55) | NR (0.95) |
| | NR (1.73) | NR (1.82) | NR (1.73) | NR (1.36) | NR (1.68) | NR (1.68) | NR (1.68) | 0.1 (1.25) |
| | NR (1.82) | | NR (1.82) | NR (1.55) | NR (1.73) | NR (1.73) | NR (1.73) | NR (1.36) |
| | 0.97 (3.35) | 0.58 (3.35) | 0.95 (3.35) | 0.13 (1.68) | NR (1.82) | NR (1.82) | NR (1.82) | 0.31 (1.55) |
| | | | | 0.39 (1.73) | NR (2.25) | NR (2.57) | NR (2.25) | NR (1.68) |
| | | | | NR (1.82) | 0.41 (3.35) | NR (2.61) | 0.46 (3.35) | 0.76 (1.73) |
| | | | | 0.24 (2.57) | | 0.35 (3.35) | | NR (1.82) |
| | | | | NR (2.61) | | | | 0.27 (2.57) |
| | | | | 0.29 (3.35) | | | | NR (2.61) |
| Total Impurity (%) | 1.59 | 1.67 | 1.62 | 2.33 | 3.28 | 5.78 | 3.24 | 5.68 |

TABLE 21

| | 60° C. | | | | | | | |
|---|---|---|---|---|---|---|---|---|
| | 10 mcg/mL ascorbic acid with oxygen scavenger (Lot # 13801-2) | | 10 mcg/mL ascorbic acid without oxygen scavenger (Lot # 13801-2) | | 50 mcg/mL ascorbic acid with oxygen scavenger (Lot # 13801-1) | | 50 mcg/mL ascorbic acid without oxygen scavenger (Lot # 13801-1) | |
| Time point | Initial | 1 Week | Initial | 1 Week | Initial | 1 Week | Initial | 1 Week |
| Appearance | CCS | CCS | CCS | CCS | CCS | CCS | CCS | CCS |
| pH | 4.03 | 4.11 | 4.03 | 4.06 | 4.05 | 4.13 | 4.08 | 4.05 |
| Dissolved Oxygen (ppm) | 1.08 | 1.02 | 7.51 | 5.99 | 1.18 | 1.10 | 7.16 | 4.92 |
| Assay (%) | 98.0 | 96.5 | 98.5 | 95.9 | 97.8 | 95.8 | 97.7 | 94.5 |
| Related substance (%) Imp-A | 0.15 | NR | 0.14 | NR | 0.13 | NR | 0.12 | NR |
| Unknown (RRT) | NR (1.36) | NR (1.35) | NR (1.36) | NR (1.35) | NR (1.36) | 0.45 (0.60) | NR (1.36) | 0.13 (0.71) |
| | 0.38 (2.33) | 0.11 (2.71) | 0.1 (2.83) | 0.11 (2.76) | NR (1.62) | NR (0.67) | NR (1.62) | NR (1.35) |
| | NR (2.83) | 0.15 (2.76) | | | 0.58 (2.83) | NR (0.82) | 0.55 (2.83) | 0.41 (2.71) |
| | | | | | | 0.48 (2.71) | | 0.55 (2.76) |
| | | | | | | 0.91 (2.76) | | |
| Total Impurity (%) | 0.52 | 0.26 | 0.24 | 0.11 | 0.71 | 1.84 | 0.67 | 1.09 |

With respect to suitable osmotic agents, various agents were considered including dextrose, mannitol and sodium chloride. Isoproterenol is subject to Maillard and Pictet-Spengler condensation in the presence of reducing sugars and as such nucleophilic degradation is expected. Dextrose is a reducing sugar that includes a reactive aldehyde moiety (reducing end) while mannitol is a sugar alcohol. However, standard excipient production of mannitol typically results in reducing sugar residues (mainly glucose). Therefore, dextrose and mannitol may pose risk of degradation especially upon terminal sterilization (autoclave). Although, the risk may be low in aseptic filling. In contrast, NaCl is an inactive ingredient that does not pose any risk of degradation to isoproterenol, and NaCl was used in further formulations for evaluation.

Various pH values were evaluated for the present formulations comprising of 0.25 mM tartrate buffer with 5 mcg/mL EDTA and sodium chloride as isotonic agent. Five pH values were assessed including pH 3.5, 4.0, 4.2, 4.5 and 5.0, and exemplary compositions are shown in Table 22. Based on the resulting osmolality, NaCl was adjusted to be 9.0 mg/mL to achieve isotonicity.

TABLE 22

| | Quantity per mL | | | | |
|---|---|---|---|---|---|
| Ingredient | Lot # 13893-1 | Lot # 13893-2 | Lot # 13893-3 | Lot # 13893-4 | Lot # 13893-5 |
| Isoproterenol hydrochloride | 4 mcg | 4 mcg | 4 mcg | 4 mcg | 4 mcg |
| L-tartaric acid | 37.5 mcg | 37.5 mcg | 37.5 mcg | 37.5 mcg | 37.5 mcg |
| Edetate disodium dihydrate (EDTA) | 5.0 mcg | 5.0 mcg | 5.0 mcg | 5.0 mcg | 5.0 mcg |
| Sodium chloride | 8.9 mg | 8.9 m | 8.9 mg | 8.9 mg | 8.9 mg |
| 10N NaCl/ 6N HCl | q.s. pH 3.5 | q.s. pH 4.0 | q.s. pH 4.2 | q.s. pH 4.5 | q.s. pH 5.0 |
| Water for injection | q.s. 1 mL | q.s. 1 mL | q.s. 1 mL | q.s. 1 mL | q.s. 1 mL |

In this series of tests, sterilization was conducted by packaging the polypropylene bag in an aluminum overwrap containing an autoclavable oxygen scavenger, heat sealing, and followed by autoclaving via AOP at 121° C. for 30 minutes exposure time. Typical results are shown in the experimental data of Table 23 and Table 24, indicating suitable pH values of pH 3.5-4.2. Assay values for solutions containing 0.25 mM tartrate buffer and 5 mcg/mL EDTA at pH 3.5, pH 4.0 and pH 4.2 on accelerated storage conditions of 60° C. demonstrated stability (100%±1%) even after two weeks. Degradation was observed for solutions at pH 4.5 and 5.0.

TABLE 23

| | | 60° C. | | | | | | | | |
|---|---|---|---|---|---|---|---|---|---|---|
| | | pH 3.5 (Lot # 13893-1) | | | pH 4.0 (Lot # 13893-2) | | | pH 4.2 (Lot # 13893-3) | | |
| Time point | | Initial | 1 Week | 2 Week | Initial | 1 Week | 2 Week | Initial | 1 Week | 2 Week |
| Appearance | | CCS | CCS | CCS | CCS | CCS | CCS | CCS | CCS | CCS |
| pH | | 3.52 | 3.54 | 3.49 | 4.05 | 3.95 | 4.00 | 4.18 | 4.15 | 4.22 |
| Dissolved Oxygen (ppm) | | 1.50 | 1.02 | 1.15 | 1.06 | 1.63 | 1.01 | 1.58 | 0.99 | 1.17 |
| Osmolality (mOsm/kg) | | 282 | 282 | 280 | 279 | 281 | 279 | 280 | 280 | 282 |
| Assay (%) | | 100.7 | 100.5 | 100.5 | 100.9 | 100.1 | 100.0 | 100.3 | 100.3 | 99.4 |
| Related substance (%) | Imp-A | NR | NR | NR | NR | NR | NR | NR | NR | NR |
| | Unknown (RRT) | NR (1.35) | NR (1.35) | NR (1.35) | NR (1.35) | NR (1.35) | NR (1.35) | NR (1.35) | NR (1.35) | NR (1.35) |
| | | NR (1.62) | 0.30 (1.47) | 0.48 (1.47) | NR (1.47) | 0.38 (1.47) | 0.50 (1.47) | NR (1.62) | 0.28 (1.47) | 0.55 (1.47) |
| | | 0.11 (1.73) | 0.17 (1.62) | 0.22 (1.62) | 0.17 (1.62) | 0.37 (1.62) | 0.42 (1.62) | NR (1.73) | 0.34 (1.62) | 0.56 (1.62) |
| | | 0.58 (3.35) | 0.20 (1.73) | 0.17 (1.73) | NR (1.73) | NR (1.73) | NR (1.73) | 1.17 (3.35) | NR (1.73) | NR (1.73) |
| | | | 0.51 (3.35) | 0.10 (2.95) | 0.88 (3.35) | 0.86 (3.35) | NR (2.71) | | 1.19 (3.35) | NR (2.71) |
| | | | | 1.33 (3.35) | | | NR (2.85) | | | 0.11 (2.95) |
| | | | | | | | 0.11 (2.95) | | | 1.97 (3.35) |
| | | | | | | | 1.60 (3.35) | | | |
| Total Impurity (%) | | 0.69 | 1.18 | 2.30 | 1.05 | 1.60 | 2.78 | 1.17 | 1.81 | 3.18 |

TABLE 24

| | 60° C. | | | | | |
|---|---|---|---|---|---|---|
| | pH 4.5 (Lot # 13893-4) | | | pH 5.0 (Lot # 13893-5) | | |
| Time point | Initial | 1 Week | 2 Week | Initial | 1 Week | 2 Week |
| Appearance | CCS | CCS | CCS | CCS | CCS | CCS |
| pH | 4.48 | 4.45 | 4.53 | 4.95 | 4.91 | 5.03 |
| Dissolved Oxygen (ppm) | 1.47 | 0.97 | 1.22 | 1.78 | 1.04 | 1.20 |
| Osmolality (mOsm/kg) | 280 | 280 | 279 | 281 | 282 | 282 |
| Assay (%) | 97.5 | 97.0 | 95.9 | 94.3 | 94.1 | 92.7 |
| Related substance (%) Imp-A | NR | NR | NR | NR | NR | NR |
| Unknown (RRT) | NR (1.35) | NR (1.35) | NR (1.35) | NR (1.35) | NR (1.15) | NR (1.35) |
| | NR (1.47) | 0.20 (1.47) | 0.42 (1.47) | NR (1.47) | NR (1.35) | 0.64 (1.47) |
| | 0.13 (1.62) | 0.35 (1.62) | 0.63 (1.62) | 0.23 (1.62) | 0.41 (1.47) | 1.51 (1.62) |
| | NR (1.73) | NR (1.73) | 0.15 (1.73) | 0.15 (1.73) | 1.14 (1.62) | 0.25 (1.73) |
| | 2.24 (3.35) | 1.47 (3.35) | NR (2.71) | NR (2.33) | 0.22 (1.73) | NR (2.20) |
| | | | NR (2.85) | 5.97 (3.35) | 3.92 (3.35) | NR (2.71) |
| | | | 0.23 (2.95) | 0.19 (3.37) | | NR (2.85) |
| | | | 2.80 (3.35) | | | 1.22 (2.95) |
| | | | | | | 4.61 (3.35) |
| Total Impurity (%) | 2.38 | 2.02 | 4.23 | 6.54 | 5.69 | 8.23 |

As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.). It should further be noted that the terms "prognosing" or "predicting" a condition, a susceptibility for development of a disease, or a response to an intended treatment is meant to cover the act of predicting or the prediction (but not treatment or diagnosis of) the condition, susceptibility and/or response, including the rate of progression, improvement, and/or duration of the condition in a subject.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the full scope of the present disclosure, and does not pose a limitation on the scope of the invention otherwise claimed. No language in the specification should be construed as indicating any non-claimed element essential to the practice of the claimed invention.

It should be apparent to those skilled in the art that many more modifications besides those already described are possible without departing from the full scope of the concepts disclosed herein. The disclosed subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification or claims refer to at least one of something selected from the group consisting of A, B, C . . . and N, the text should be interpreted as requiring only one element from the group, not A plus N, or B plus N, etc.

What is claimed is:

1. A storage stable sterile ready-to-administer pharmaceutical composition, comprising:
    a buffered aqueous solution comprising isoproterenol at a concentration of between 1-10 mcg/mL;
    wherein the buffered aqueous solution has a pH range of between 3.0 and 4.5 and wherein the buffer is a tartrate buffer and has a concentration of equal to or less than 10 mM;
    wherein the solution further comprises ethylenediamine tetraacetic acid (EDTA) as a chelating agent at a concentration of about 5 mcg/mL and a tonicity agent;
    wherein the ready-to-administer composition contains, after storage over at least three weeks at 60° C. in a container having a headspace that has not been flushed with an inert gas, equal to or less than 2.0% of total impurities formed from degradation of the isoproterenol, and
    wherein the composition is formulated for intravenous administration and is antioxidant free.

2. The composition of claim 1 wherein the isoproterenol is present at a concentration of 4.0±0.2 mcg/mL.

3. The composition of claim 1 wherein the buffered aqueous solution has a pH range of between 3.5 and 4.2.

4. The composition of claim 1 wherein the buffered aqueous solution has a pH of 4.0±0.2.

5. The composition of claim 1 wherein the buffer has a concentration of equal to or less than 1 mM.

6. The composition of claim 1 wherein the buffer has a concentration of 1 mM or 0.25 mM.

7. The composition of claim 1 wherein the tonicity agent is NaCl and is present in an amount of equal to or less than 9 mg/mL.

8. The composition of claim 1 wherein the tonicity agent is present in an amount that generates a tonicity between 260 and 320 mOsm.

9. The composition of claim 1 wherein the ready-to-administer composition contains, after storage over at least three weeks at 60° C., equal to or less than 1.5% of total impurities formed from degradation of the isoproterenol.

10. The composition of claim 1 wherein the ready-to-administer composition is an autoclaved composition or filter sterilized composition.

11. A kit comprising a primary container and a pharmaceutical composition disposed in the primary container, wherein the pharmaceutical composition is the storage stable sterile ready-to-administer pharmaceutical composition of claim 1, and wherein the pharmaceutical composition is present in the primary container at a volume of between 10 mL and 150 mL.

12. The kit of claim 11 wherein the primary container is disposed in a secondary container, and wherein the secondary container comprises a metal or is light impermeable.

13. The kit of claim 12 further comprising a non-contact oxygen absorber disposed in a space between the primary container and the secondary container.

14. The kit of claim 11 wherein the volume is 100 mL.

15. A method of preparing a storage stable liquid sterile ready-to administer pharmaceutical composition, comprising:
    formulating a liquid parenteral composition for intravenous administration that contains in a buffered aqueous acidic solution isoproterenol, a chelating agent, and a tonicity agent;
    wherein the buffered aqueous acidic solution has a pH range of between 3.0 and 4.5, wherein the buffer is a tartrate buffer, and wherein the buffer has a concentration of equal to or less than 10 mM;
    wherein the isoproterenol is present in the composition at a concentration of between 1 and 10 mcg/mL;
    wherein the chelating agent is ethylenediamine tetraacetic acid (EDTA) and is present at a concentration of equal to or less than 10 mcg/mL; and
    sterilizing the liquid parenteral composition via thermal sterilization to obtain the storage stable liquid sterile ready-to-administer pharmaceutical composition,
    wherein the liquid sterile ready-to-administer pharmaceutical composition contains, after storage over at least three weeks at 60° C. in a container having a headspace that has not been flushed with an inert gas, equal to or less than 2.0% of total impurities formed from degradation of the isoproterenol.

16. The method of claim 15 wherein the isoproterenol is present at a concentration of 4.0±0.2 mcg/mL, and/or wherein the buffered aqueous solution has a pH of 4.0±0.2.

17. The method of claim 15 wherein the buffer has a concentration of 1 mM or 0.25 mM, and/or wherein the chelating agent is present at a concentration of 5±2 mcg/mL.

18. The method of claim 15 further comprising a step of packaging the composition into a primary container, packaging the primary container into a secondary container, and placing a non-contact oxygen absorber in a space between the primary container and the secondary container.

* * * * *